United States Patent
Nystrom et al.

(10) Patent No.: US 8,343,098 B2
(45) Date of Patent: Jan. 1, 2013

(54) METHOD AND SYSTEM FOR REMOVING AIR FROM A FLOW PATH OF A FLUID INJECTION DEVICE

(75) Inventors: Sidney D. Nystrom, Shoreview, MN (US); David J. Hajicek, Minnetonka, MN (US); Touhid Khan, Eden Prairie, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 682 days.

(21) Appl. No.: 12/494,011

(22) Filed: Jun. 29, 2009

(65) Prior Publication Data

US 2010/0331779 A1  Dec. 30, 2010

(51) Int. Cl.
*A61M 1/00* (2006.01)
*A61M 37/00* (2006.01)

(52) U.S. Cl. .................. 604/123; 604/122; 604/152

(58) Field of Classification Search .............. 604/118, 604/121, 122, 131, 151, 152, 123; 64/123
See application file for complete search history.

(56) References Cited

U.S. PATENT DOCUMENTS

| | | | |
|---|---|---|---|
| 2,627,270 A | 2/1953 | Glass | |
| 5,573,515 A | 11/1996 | Wilson et al. | |
| 5,800,397 A | 9/1998 | Wilson et al. | |
| 5,882,343 A | 3/1999 | Wilson et al. | |
| 6,050,450 A | 4/2000 | Gardos | |
| 6,099,502 A | 8/2000 | Duchon et al. | |
| 6,221,045 B1 | 4/2001 | Duchon et al. | |
| 6,344,030 B1 | 2/2002 | Duchon et al. | |
| 6,447,481 B1 | 9/2002 | Duchon et al. | |
| 6,656,157 B1 | 12/2003 | Duchon et al. | |
| 6,733,477 B2 | 5/2004 | Cowan et al. | |
| 6,746,427 B2 | 6/2004 | Duchon et al. | |
| 6,752,789 B2 | 6/2004 | Duchon et al. | |
| 6,945,959 B2 | 9/2005 | Duchon et al. | |
| 7,094,216 B2 | 8/2006 | Trombley, III et al. | |
| 7,128,729 B2 | 10/2006 | Duchon et al. | |
| 7,153,288 B2 | 12/2006 | Duchon et al. | |
| 7,267,666 B1 | 9/2007 | Duchon et al. | |
| 7,326,186 B2 | 2/2008 | Trombley, III et al. | |
| 7,357,785 B2 | 4/2008 | Duchon et al. | |
| 7,389,788 B2 | 6/2008 | Wilson et al. | |
| 7,566,326 B2 | 7/2009 | Duchon et al. | |
| 7,617,837 B2 | 11/2009 | Wilson et al. | |
| 7,662,124 B2 | 2/2010 | Duchon et al. | |
| 7,703,483 B2 | 4/2010 | Hartman et al. | |
| 2006/0079768 A1* | 4/2006 | Small et al. | 600/432 |
| 2006/0180202 A1 | 8/2006 | Wilson et al. | |
| 2007/0055202 A1* | 3/2007 | Duchon et al. | 604/110 |

(Continued)

OTHER PUBLICATIONS

PCT/US2010/040333, International Search Report and Written Opinion dated Sep. 1, 2010, 9 pages.

*Primary Examiner* — Nicholas D Lucchesi
*Assistant Examiner* — Leah Stohr
(74) *Attorney, Agent, or Firm* — Fredrikson & Byron, P.A.

(57) ABSTRACT

A method of removing air from a flow path of a medical fluid injection system is described. An exemplary method performed by the medical fluid injection device includes delivering a first amount of fluid to a fluid flow path, isolating fluid flow along the flow path, forming a vacuum condition upstream of the fluid isolation, re-establishing fluid communications along the flow path, and delivering a second amount of fluid to the flow path.

38 Claims, 16 Drawing Sheets

U.S. PATENT DOCUMENTS

| | | |
|---|---|---|
| 2008/0091142 A1 | 4/2008 | Trombley, III et al. |
| 2008/0103437 A1 | 5/2008 | Duchon et al. |
| 2008/0183131 A1 | 7/2008 | Duchon et al. |
| 2009/0149743 A1 | 6/2009 | Barron et al. |
| 2009/0221914 A1 | 9/2009 | Barrett et al. |
| 2009/0312740 A1 | 12/2009 | Kim et al. |
| 2010/0019178 A1 | 1/2010 | Wilson et al. |
| 2010/0113924 A1 | 5/2010 | Hajicek et al. |

* cited by examiner

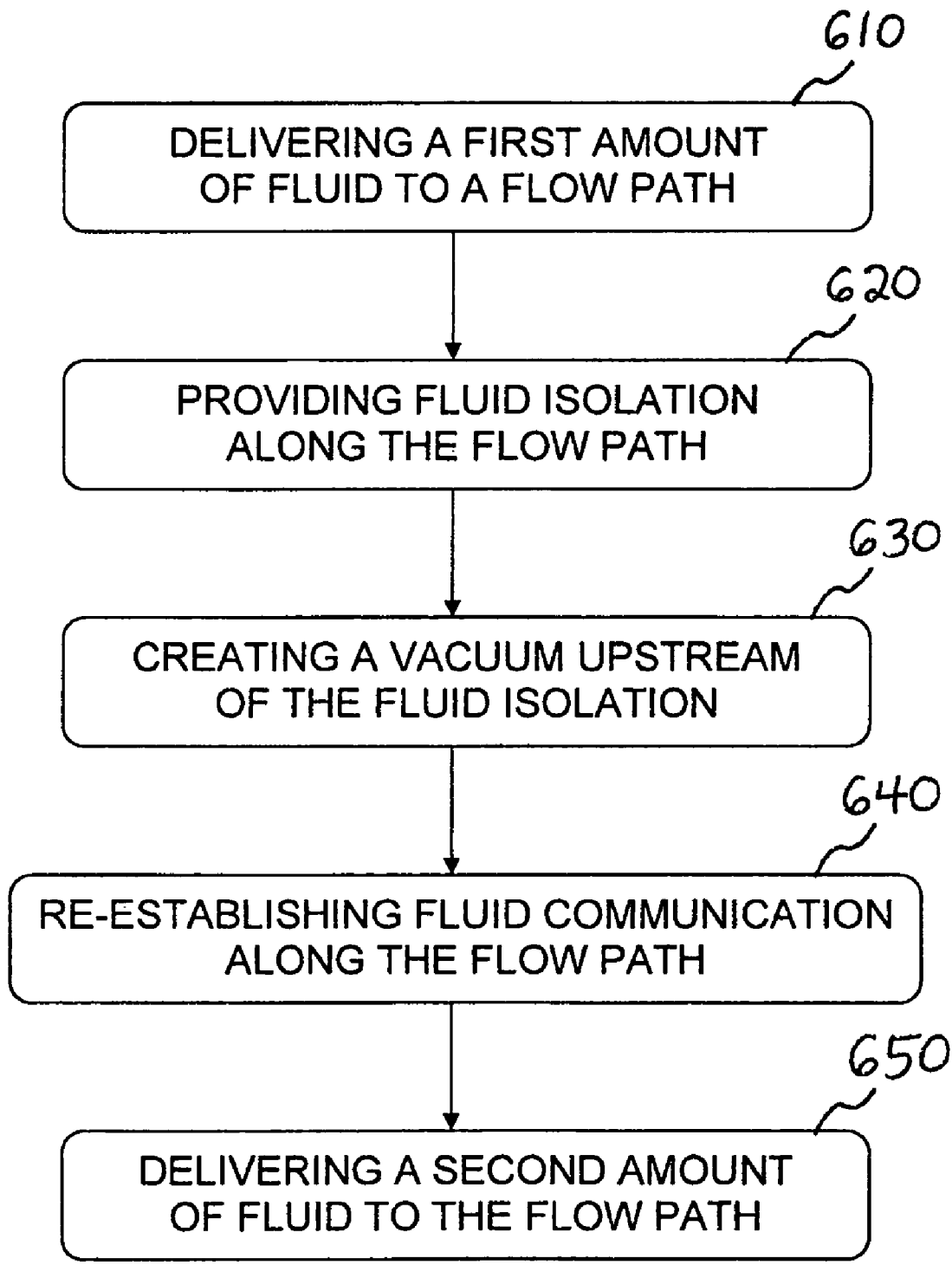

METHOD AND SYSTEM FOR REMOVING AIR FROM A FLOW PATH OF A FLUID INJECTION DEVICE

TECHNICAL FIELD

This disclosure relates generally to the use of medical fluid injection devices, and more particularly, to a method of removing air from one or more flow paths associated with such devices.

BACKGROUND

Medical fluid injection devices are typically used to inject a medical fluid, such as saline or contrast media, into a patient. These devices often include one or more reservoirs to hold the medical fluid, and one or more pressurizing units to inject the medical fluid into the patient. For example, a contrast media powered injection device may include a reservoir containing contrast media and a syringe that is used to inject the contrast media into the patient. The contrast media injection device may be used during certain medical procedures, such as angiographic or computed tomography (CT) or magnetic resonance imaging (MRI) procedures.

Many medical fluid injection devices include one or more pressurizing units (e.g., syringes, pumps, etc.) to inject fluid. A syringe, for example, may have a chamber for holding the fluid and a plunger that is moveable within the chamber. The fluid is typically drawn into the chamber from a fluid reservoir when the plunger is moved in a first direction (e.g., retracted). The fluid may subsequently be expelled from the chamber and into the patient, for example via a catheter, when the plunger is moved in a second, opposite direction (e.g., advanced). The fluid is expelled or delivered at a rate (e.g., a flow rate, typically measured in units of volume per unit of time) that may be determined by a speed of movement of the plunger.

A medical fluid injection device or system may include one or more fluid connectors to establish fluid flow paths between the injection device and the patient, and between various portions of the device/system. For example, some portions of a medical fluid injection system may include disposable components (e.g., sterile tubing), while other portions of the system may comprise reusable components designed for repeated uses (e.g., for multiple patients, or for multiple procedures). Certain disposable components may be further categorized as single-use or multiple-use components, for example. Establishing fluid connections between the various components of a fluid injection system may involve the use of fluid connectors adapted to facilitate making the connections (e.g., to make it relatively easy for an operator to make the connection), while also ensuring appropriate or adequate fluid properties around the site of the connections (e.g., air tight seal, no leaks in or out, etc.). In some cases, such fluid connectors may include a sealing component adapted to establish a fluid seal (e.g., to prevent leaks near the site of the fluid connection). The sealing component may employ a frictional or compressive aspect, for example, to achieve the fluid seal. O-rings, gaskets, and certain elastomeric fittings are examples of sealing components which may employ a frictional or compressive aspect to achieve a fluid seal in a fluid connector.

For patient safety, a medical fluid injection system may incorporate safety features and/or operating procedures designed to prevent the inadvertent injection of air into a patient. Safety features might include, for example, the ability of the medical fluid injection system to detect the presence of air or air bubbles in the medical fluid to be injected. The detection of air in the fluid may trigger a response, such as an audible or visible alarm to alert an operator, and/or an automatic termination of an injection, for example. An acoustic sensor (e.g., an ultrasonic sensor) is one example of an air detector that could be used to detect the presence of air in the fluid flow path. Operating procedures might include, for example, actions taken manually or automatically by the medical fluid injection system. For example, prior to a medical fluid injection into a patient, a purge procedure may be performed. A purge procedure might typically involve flushing fluid through the fluid flow path, thereby causing air that may exist in the fluid flow path to be pushed through and out of the flow path prior to establishing fluid flow to a patient. This could be done, for example, by using the medical fluid injection system to push or flush fluid through the system as part of a procedure, for example, in conjunction with filling the pressurizing unit with the medical fluid to be delivered.

SUMMARY

In general, this disclosure relates to methods, devices, and systems for removing air from a flow path of a medical fluid injection system, and computer readable media associated with such methods, devices, and systems.

In some embodiments, a method for removing air from a flow path of a medical fluid injection system may include establishing the flow path using a fluid connector, delivering a first amount of a medical fluid to the flow path, providing fluid isolation along the flow path, creating a vacuum, removing the fluid isolation, and delivering a second amount of medical fluid to the flow path. In some embodiments of the invention, the flow path is established by placing a downstream fluid portion in fluid connection with an upstream fluid portion via a fluid connector disposed therebetween, the upstream fluid portion being in fluid communication with a pressurizing unit of the medical fluid injection system. In some embodiments of the invention, fluid isolation is provided along the upstream fluid portion, and the vacuum is created in the pressurizing unit. Removing the fluid isolation then exposes the fluid connector to the lower pressure vacuum condition, which may cause air bubbles to expand and move to a location where they may be subsequently removed from the flow path (e.g., upon delivering the second amount of medical fluid).

In some embodiments, an exemplary medical fluid injection system may be adapted to remove air from a flow path of the medical fluid injection system. Such a fluid injection system may, for example, comprise: an injector head having a source of motive force and an internal processor adapted to carry out instructions, the injector head being adapted to receive a pressurizing unit and further adapted to provide the motive force to cause the pressurizing unit to receive and/or expel fluid; a proximal fluid conduit operably engaged with an outlet of the pressurizing unit, the proximal fluid conduit being adapted to be placed in fluid communication with a distal fluid conduit via a fluid connector, thereby establishing a flow path; and a valve for providing fluid isolation along the flow path.

In some embodiments, a computer readable medium may embody computer readable instructions for causing a fluid injection system to perform a method of removing air from a flow path of the fluid injection system, the method comprising: delivering a first amount of a medical fluid to the flow path, providing fluid isolation along the flow path, creating a vacuum, removing the fluid isolation, and delivering a second amount of medical fluid to the flow path.

The details of one or more embodiments are set forth in the accompanying drawings and the description below. Other features, objects, and advantages will be apparent from the description and drawings, and from the claims.

BRIEF DESCRIPTION OF DRAWINGS

FIG. 6 is a flow diagram of a method that may be performed by a powered medical fluid injection device to remove air from a flow path, according to one embodiment.

DETAILED DESCRIPTION

Figure 1A:
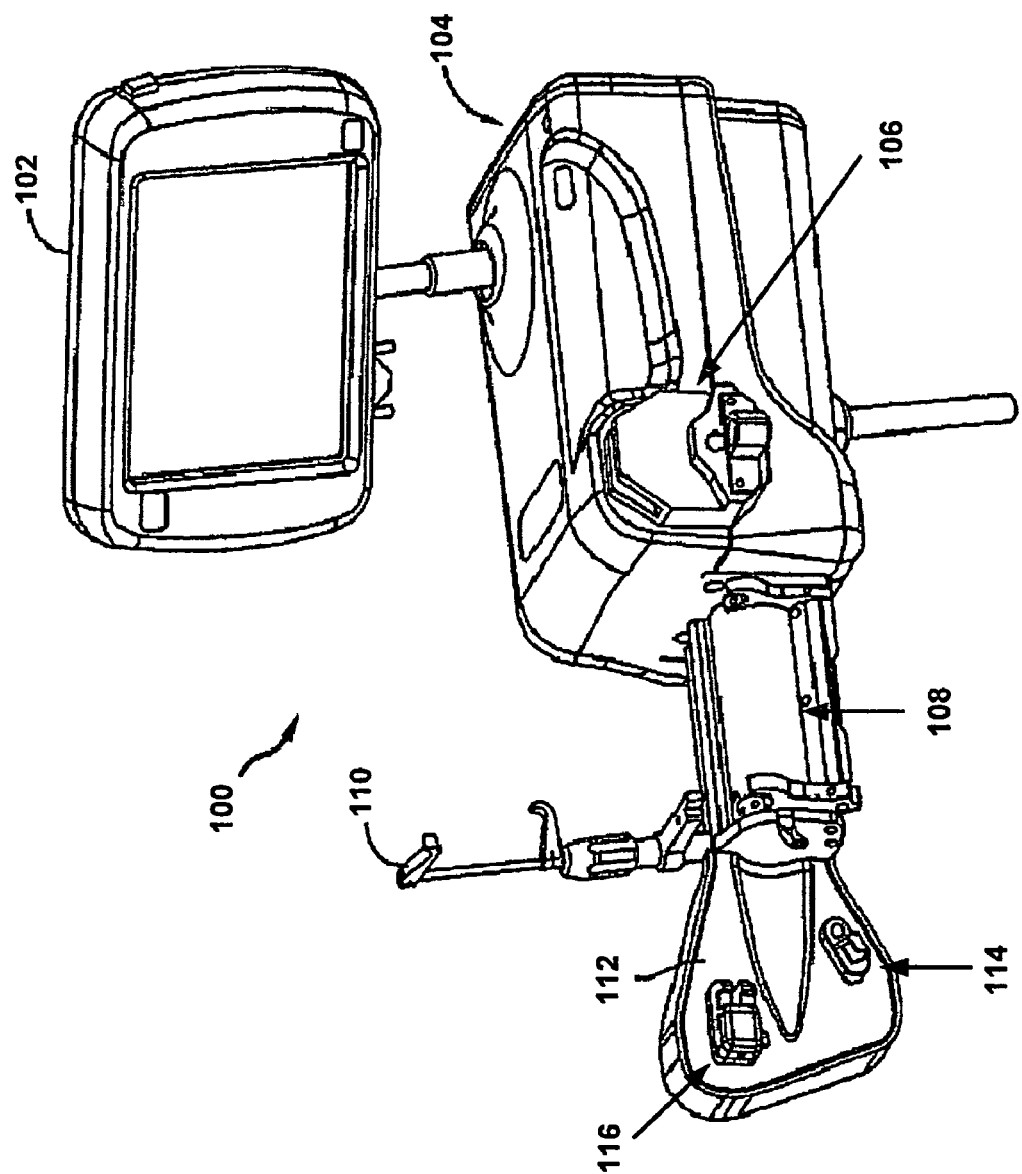
FIG. 1A is a perspective diagram of one embodiment of a powered medical fluid injection device that may be used to automatically supply a pressurizing unit with fluid.

FIG. 1A is a perspective diagram of one embodiment of a powered medical fluid injection device 100 that may be used to remove air from a fluid flow path, according to some embodiments of the invention. Injection device 100 may be adapted to house or support a pressurizing unit within a sleeve 108, the pressurizing unit being adapted to hold a medical fluid such as a contrast medium or saline solution. In the embodiment of FIG. 1A, the pressurizing unit within sleeve 108 is a syringe. In other embodiments, other forms of pressurizing units may be used, including various types of positive displacement pumps, for example.

Figure 3:
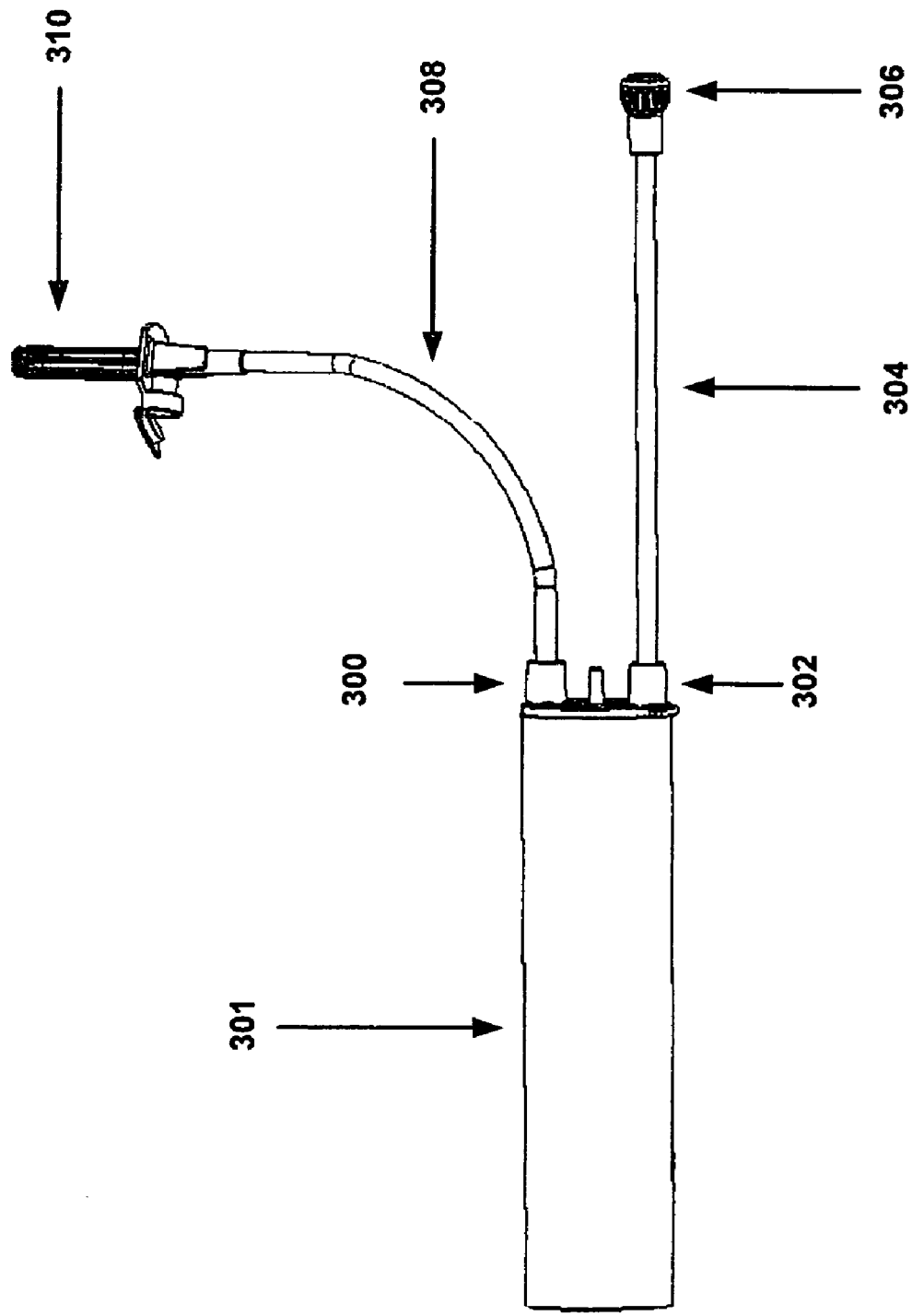
FIG. 3 is a perspective diagram of an example syringe that may be used as a pressurizing unit with a powered medical fluid injection device, according to one embodiment.

Device 100, according to some embodiments, may be used to inject a medical fluid, such as contrast media or saline, into a patient during a medical procedure. Exemplary medical procedures may include angiographic procedures, computed tomography (CT) procedures, magnetic resonance imaging (MRI) procedures, and other forms of diagnostic imaging procedures, for example. Device 100 depicted in FIG. 1A includes control panel 102, injector head 104, sleeve 108 to hold a pressurizing unit (e.g., a syringe, not visible in FIG. 1A), reservoir holder 110, module 112, patient manifold sensor 114, and air detector 116. Injector head 104 includes a pump 106 and also includes one or more processors used to control and/or monitor injector head 104, control panel 102, the pressurizing unit within sleeve 108, pump 106, patient manifold sensor 114, and air detector 116 of device 100. Reservoir holder 110 is capable of holding a fluid reservoir that contains a fluid that may be drawn into the pressurizing unit during operation of device 100. For example, reservoir holder 110 may hold a reservoir of contrast media or diluent. Typical fluid reservoirs include bottles and bags, for example. A second reservoir holder (not shown) may hold a second fluid, such as a diluent (e.g., saline). A second fluid may be delivered, for example, via operation of pump 106, according to some embodiments. FIG. 3 shows an example of a syringe that may be used as a pressurizing unit within sleeve 108, according to some embodiments. Patient manifold sensor 114 may, in some cases, be connected to a patient manifold, as will be described in more detail with reference to FIG. 1B.

An operator of device 100, such as a physician/clinician, may use control panel 102 to set up various parameters and/or protocols to be used for a given fluid injection procedure. For example, the operator may interact with control panel 102 to enter injection parameters such as flow rate, maximum injection volume, maximum injection pressure, rise time, and/or other injection parameters. In one embodiment, control panel 102 includes a touch-screen panel display, enabling an operator to view and modify injection parameters as desired. Control panel 102 may also be used to initialize device 100 (e.g., to prepare it for a patient fluid injection), or to activate certain features or sequences of operations of device 100.

Pump 106 is capable of pumping fluid. In the embodiment shown in FIG. 1A, pump 106 is a peristaltic pump. In this embodiment, tubing and a fluid reservoir (not shown) are coupled to and through pump 106. Pump 106 pumps fluid from the fluid reservoir through the tubing towards module 112. In the example of FIG. 1A, both pump 106 and the syringe contained within sleeve 108 are capable of delivering fluid from device 100 into a catheter. Pump 106 may be driven by a motor that is part of pump 106, for example. The syringe contained within sleeve 108 houses a plunger adapted to be driven (e.g., advanced and/or retracted within the syringe) by a motor assembly, including an actuator, which is part of injector head 104. In one embodiment, injector head 104 includes a processor that controls the operation of the motor assembly.

In one embodiment, reservoir holder 110 holds a fluid reservoir that is coupled to input fluid tubing. This input fluid tubing (or input tubing) may be coupled to the syringe within sleeve 108 such that, when a plunger within the syringe is moved in a first direction by the motor assembly and/or actuator, fluid is drawn from the fluid reservoir into the syringe. The syringe within sleeve 108 may also be coupled to output tubing. When the plunger within the syringe is moved in a second direction (e.g., opposite the first direction), fluid within the syringe is thereby expelled out of the syringe and into the output tubing. In one embodiment, the syringe is a dual-port syringe, such that the input tubing is coupled to one port of the syringe, and the output tubing is coupled to a second port of the syringe. FIG. 3 shows an example of such a dual-port syringe, which will be described in more detail below.

Patient manifold sensor 114 is coupled to a manifold valve (not shown), according to one embodiment. This manifold valve may be used to control the flow of fluid being delivered from either the syringe in sleeve 108 or pump 106 (typically, via tubing coupling the manifold valve to either the syringe in sleeve 108 or pump 106). In one embodiment, the manifold valve has two inlet ports and an outlet port. One inlet port is coupled to output tubing from the syringe, and a second inlet port is coupled to tubing that runs through pump 106. Tubing also is coupled between the outlet of the manifold valve and air detector 116. After passing through air detector 116, the tubing is then coupled to a patient line or catheter (not shown), such that fluid can ultimately be delivered from device 100 to a patient.

The manifold valve held by the patient manifold sensor 114 is capable of controlling the flow of fluid from the syringe and pump 106 to a patient catheter. In one embodiment, the manifold valve has a first position that allows only fluid from the syringe to be delivered to the catheter, and a second position that allows only fluid from pump 106 to be delivered to the catheter. In one embodiment, the manifold valve may comprise a spring-biased spool valve, but in other embodiments, other types of valves, including check valves, may also be used. Patient manifold sensor 114 can detect the manifold valve position and report this position to injector head 104 for monitoring, control, and/or safety purposes.

Device 100 may include air detector 116, as shown in FIG. 1A. Tubing that runs from device 100 to an external (patient) catheter passes through air detector 116, which is capable of detecting air bubbles or air columns within the tubing. If air detector 116 detects a measurable (or otherwise significant) amount of air within the tubing, it is capable of generating a signal and sending the signal to injector head 104. In such a case, a warning or alarm message may be displayed to the operator on control panel 102 indicating that air has been detected. In addition, in some embodiments, device 100 may automatically pause or terminate a fluid injection procedure if air detector 116 has detected air in the tubing, to prevent air from being delivered to the catheter (and hence, to the patient).

Because device 100 may be used for many injections and patient procedures, injection fluids may need to be replaced frequently. For example, when the fluid reservoir held by reservoir holder 110 becomes empty, it may need to be manually replaced with a new (full) reservoir by the operator. In addition, the syringe in sleeve 108 may need to be supplied with injection fluid from time to time, such that there is sufficient fluid within the syringe to perform injections for patient procedures. When an operator detects that a fluid volume within the syringe has decreased to a sufficiently low level, the operator may initiate a manual fluid replenishment procedure by pressing or touching a button on control panel 102, or otherwise interacting with control panel 102. By doing so, the operator may manually cause the syringe to be supplied with fluid from the fluid reservoir, either partially or completely.

Figure 1B:
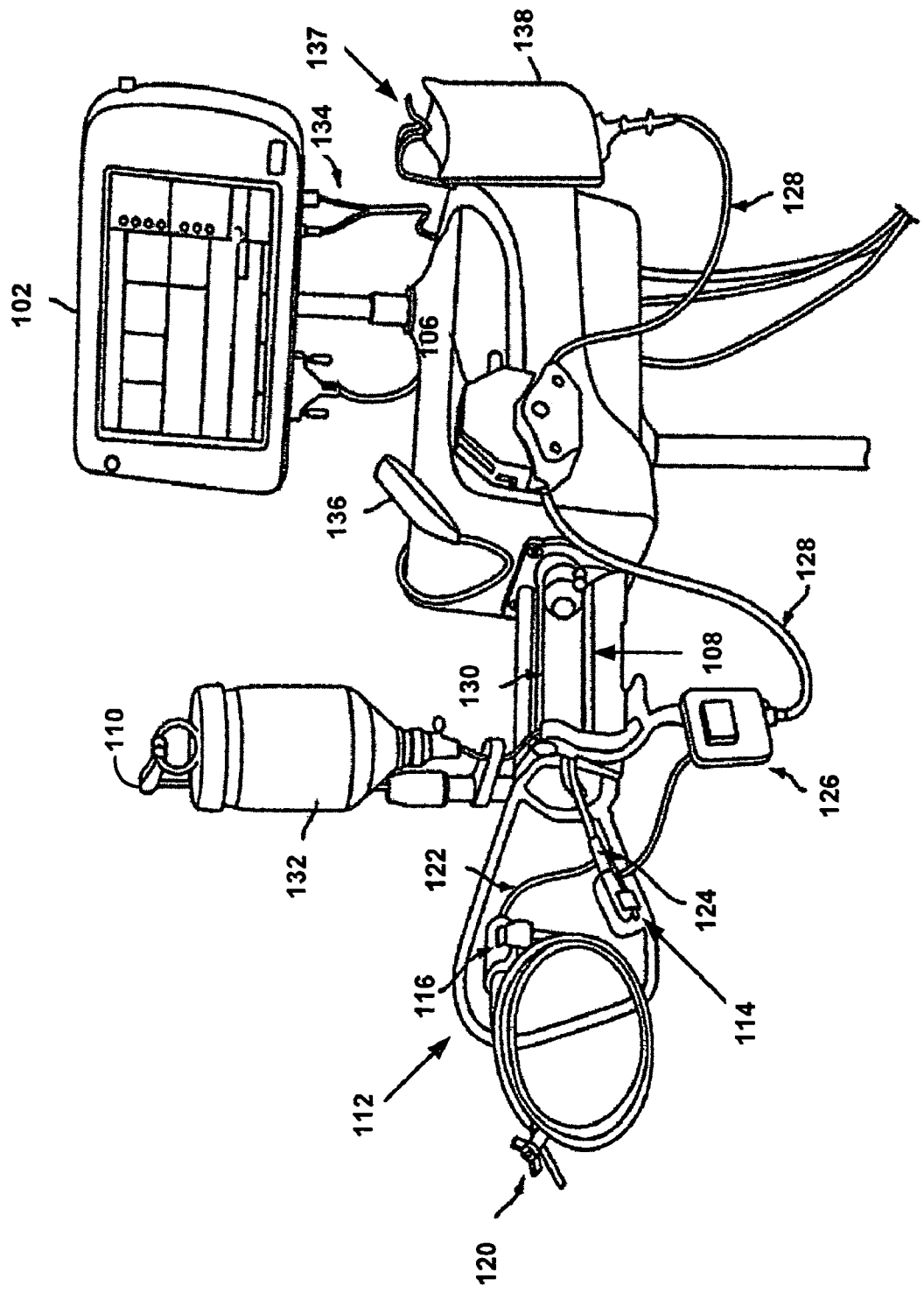
FIG. 1B is a perspective diagram of one embodiment of the powered medical fluid injection device of FIG. 1A connected to various components, including fluid reservoirs and tubing.

FIG. 1B is a perspective diagram of one embodiment of the powered medical fluid injection device 100 of FIG. 1A connected to various components, including fluid reservoirs and associated tubing. For example, FIG. 1B shows a first fluid reservoir 132 and a second fluid reservoir 138. First fluid reservoir 132 contains a first fluid, such as contrast media. An operator may hang first fluid reservoir 132 on reservoir holder 110. In some cases, first fluid reservoir 132 may be a glass reservoir, such as a glass bottle, while in other cases, it may be a plastic reservoir, such as a plastic bag. The fluid contained within first fluid reservoir 132 may be drawn through tubing and into a pressurizing unit 130 (e.g., a syringe) that has been inserted into sleeve 108. Some embodiments may be adapted to perform automatic replenishment operations, during which device 100 may automatically supply pressurizing unit 130 with an amount of fluid from first fluid reservoir 132.

Second fluid reservoir 138 may contain a second fluid, such as saline. An operator may hang second fluid reservoir 138 on a hook 137. In some cases, second fluid reservoir 138 may be a plastic reservoir, such as a bag. The fluid contained within second fluid reservoir 138 may be drawn through tubing 128 through operation of pump 106.

The fluid injection system depicted in FIG. 1B also shows a hand-control device 136 coupled to control panel 102 via a connector 134. In some embodiments, hand-control device 136 may be connected to another component of device 100 other than control panel 102, such as injector head 104. As shown in FIG. 1B, hand-control device 136 is coupled to tubing, cabling, or wiring, which connects hand-control device 136 to connector 134, and which allows signals generated by hand-control device 136 to be transmitted or communicated via connector 134. Connector 134 may then be connected to or disconnected from control panel 102, for example, or to some other component of device 100. An operator may manipulate hand-control device 136 to control injection of fluid from device 100. For example, the operator may use hand-control device 136 as a variable-rate control device to variably control the rate of flow of fluid from device 100 (e.g., flow of fluid out of pressurizing unit 130). In some embodiments, hand-control device 136 may comprise an electrical device (e.g., capable of generating and transmitting an electrical signal via connector 134). In some embodiments, hand-control device 136 may comprise a pneumatic device (e.g., capable of generating and transmitting a pneumatic signal via connector 134).

Tubing 128, as shown in FIG. 1B, may be coupled to a pressure transducer 126. Pressure transducer 126 is coupled to tubing 122, which may comprise high-pressure tubing, and which may be connected to a patient line via connector 120, substantially as shown. When high-pressure tubing 122 is connected to a patient line (within a patient), pressure transducer 126 is capable of functioning as a hemodynamic monitor for the patient. Pressure transducer 126 converts detected pressures into electrical signals that may be monitored or otherwise used by device 100 or another monitoring device. High-pressure tubing 122 also runs through air detector 116. As noted above, air detector 116 is capable of detecting the presence of air (e.g., air bubbles or air columns) within fluid that may be flowing through high-pressure tubing 122.

FIG. 1B also shows a manifold valve 124. Manifold valve 124 has an outlet port connected to high-pressure tubing 122. Manifold valve 124 is held by patient manifold sensor 114, which is adapted to sense the position of manifold valve 124. Manifold valve 124 is capable of controlling the flow of fluid from pressurizing unit 130 and/or through pump 106 to high-pressure tubing 122. For example, in one embodiment, when manifold valve 124 is in a first position, fluid may flow from pressurizing unit 130 to high-pressure tubing 122. When manifold valve 124, however, is in a second position, fluid may flow through pump 106, via tubing 128, to high-pressure tubing 122. In one embodiment, manifold valve 124 may allow fluid flow to high-pressure tubing 122 from only one of the two sources (e.g., pressurizing unit 130 or pump 106) at a time.

Figure 2A:
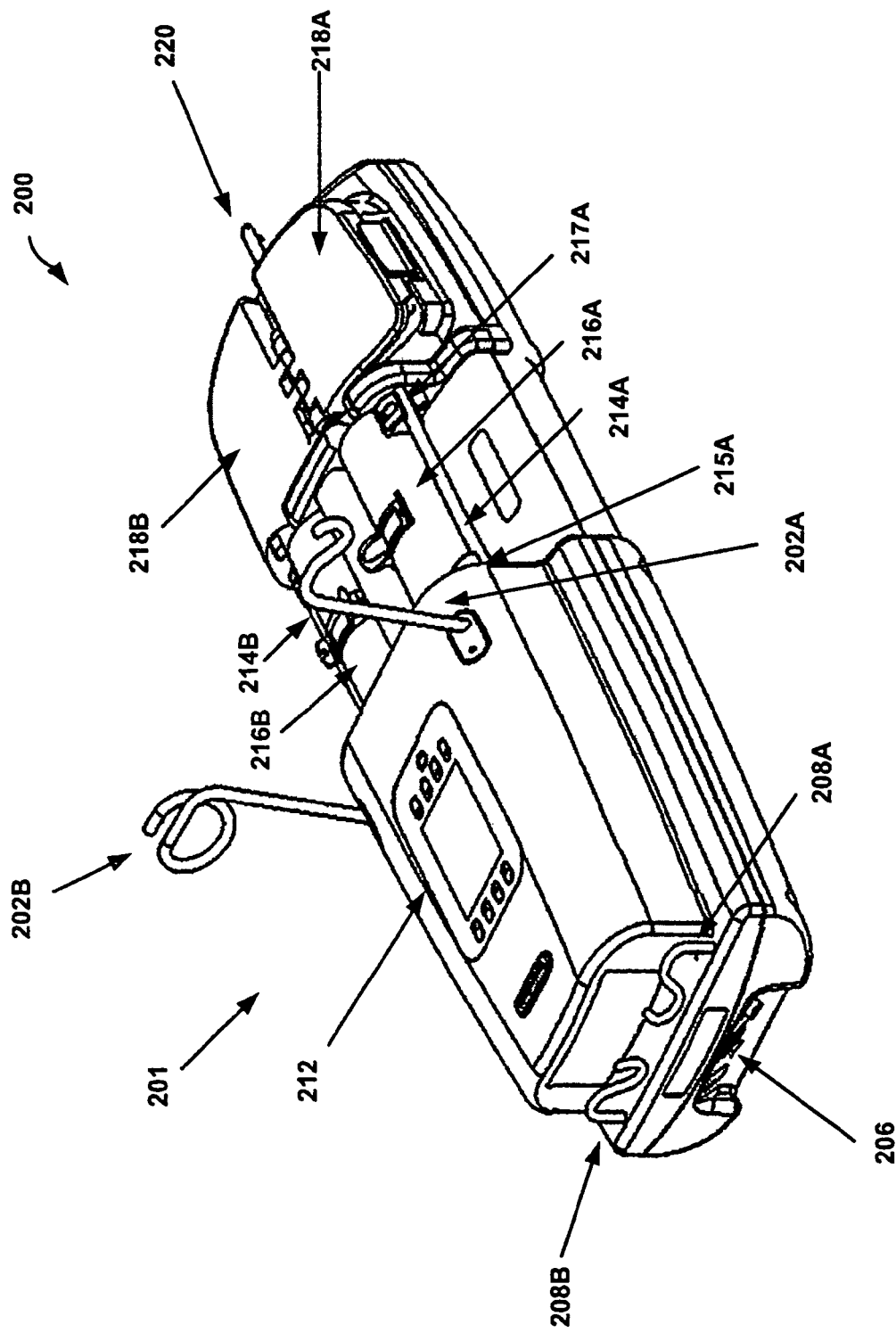
FIGS. 2A-2D are various perspective diagrams of another embodiment of a powered medical fluid injection device that may be used to automatically supply one or more pressurizing units with fluid.

FIG. 2A is a perspective diagram of another embodiment of a powered fluid injection device 200. In FIG. 2A, device 200 includes a first primary reservoir holder 202A, a second primary reservoir holder 202B, a connection interface 206, a first backup reservoir holder 208A, a second backup reservoir holder 208B, a control panel 212, a first syringe rod 214A, a second syringe rod 214B, a first syringe sleeve 216A, a second syringe sleeve 216B, a first front-end assembly 218A, a second front-end assembly 218B, and a connection guide rod 220. In the particular embodiment of FIG. 2A, the pressurizing units used to deliver medical fluid are syringes contained within syringe sleeves 216A and 216B. Injector head 201 may house, support, or otherwise include reservoir holders 202A, 202B, 208A, and 208B, connection interface 206, and control panel 212. Injector head 201 may further include one or more processors adapted to control and/or monitor the components of injector head 201 and other components of device 200.

Reservoir holder 202A is capable of holding a first reservoir of medical fluid, while reservoir holder 202B is capable of holding a second reservoir of medical fluid. In one embodiment, reservoir holder 202A holds a reservoir of a first type of fluid, such as contrast media, while reservoir holder 202B holds a reservoir of a second fluid, typically a different type of fluid, such as a diluent (e.g., saline). Different forms of reservoirs (e.g., bottles, bags) may be used with reservoir holders 202A and 202B. Because device 200 may be used to inject medical fluid spanning multiple patient procedures, the reservoirs held by holders 202A and 202B may need to be replaced periodically. Typically, an operator of device 200 manually replaces the reservoirs on holders 202A and 202B. For operator convenience, device 200 additionally includes backup holders 208A and 208B. The operator may store backup fluid reservoirs on holders 208A and 208B. When a reservoir on primary holder 202A or 202B runs empty and needs to be replaced, operator may quickly and easily access a new fluid reservoir from one of backup holders 208A or 208B and attach to primary holder 202A or 202B.

Device 200 includes connection interface 206, which may be used to directly or indirectly couple device 200 to an external device, such as a medical imaging device, for example. Typically, device 200, when used as a contrast media injection device, works in conjunction with a medical imaging device. For example, device 200 may work in conjunction with a medical imaging device during an angiographic or CT procedure. Connection interface 206 is used to directly or indirectly connect device 200 to such an imaging device. In one embodiment, device 200 may transmit injection and/or control information to an external imaging device via interface 206, and may receive imaging and/or control information from the external imaging device via interface 206, as well.

FIG. 2A shows that device 200 also includes control panel 212. Control panel 212 is located on a top side or surface of example device 200. The operator may interact with control panel 212 to program various injection procedure parameters and/or protocols that may be used for injection procedures. The operator may also use control panel to set up device 200 for use, to begin, pause, resume, or end a procedure, or to view various injection-related information (such as flow rate, volume, pressure, rise time, procedure type, fluid information, and/or patient information). FIG. 2A shows various user-activated buttons on the side of control panel 212. However, in one embodiment, control panel 212 may include a touch-activated screen.

In one embodiment, a separate, larger control panel (not shown in FIG. 2A) may also be in communication with device 200. In this embodiment, the larger control panel provides similar operator functionality to that provided by control panel 212. However, the larger control panel may be mounted to a rail of a bed on which a patient is lying, or may be mounted to other devices separate from device 200. In one embodiment, the larger control panel looks similar to control panel 102 shown in FIG. 1A.

Device 200 is a dual-syringe device that includes two syringes contained within syringe sleeves 216A and 216B. Both syringes are capable of delivering medical fluid to a patient. Syringe rod 214A, which is part of device 200, couples sleeve 216A to device 200, while syringe rod 214B couples sleeve 216B to device 200. Sleeve 216A includes connectors 215A and 217A which connect sleeve 216A to rod 214A. Connectors 215A and 217A are attached to sleeve 216A, according to one embodiment, and allow sleeve 216A to be attached or removed from rod 214A. In one embodiment, connectors 215A and 217A allow sleeve 216A to be rotated about the axis of rod 214A. Thus, in this embodiment, an operator may rotationally load and unload sleeve 216A from device 200 without detaching sleeve 216A from rod 214A. (FIG. 2A shows sleeve 216A in the loaded position, in which a syringe has been inserted into sleeve 216A.) When the operator wishes to remove the syringe contained within sleeve 216A from device 200, the operator may move sleeve 216A to an unloaded position by rotating it about rod 214A, and may then remove the syringe contained within sleeve 216A by sliding it out of sleeve 216A. If the operator further wishes to remove sleeve 216A from device 200, the operator may detach connectors 215A and 217A from rod 214A (such as by rotating sleeve 216A to an unload position and manually pulling sleeve 216A away from rod 214A). In one embodiment, the syringe contained within sleeve 216A is a disposable component that may be disposed of and replaced after use in one or more patient procedures. Sleeve 216B includes connectors 215B and 217B (shown in FIG. 2C) which connect sleeve 216B to rod 214B. A separate syringe may be contained within sleeve 216B.

In one embodiment, the syringe within sleeve 216A is capable of drawing in fluid from a fluid reservoir coupled to holder 202A, and the syringe within sleeve 216B is capable of drawing in fluid from a fluid reservoir coupled to holder 202B. For example, these syringes may draw in fluid during initial set-up of device 200, or during a subsequent fluid replenishment operation, for example. Each syringe is coupled to a motor/actuator assembly (not shown) capable of moving or driving a plunger within the respective syringe. The motor/actuator assembly is adapted to drive the plunger in two directions (e.g., forward and backward, or distally and proximally) along a longitudinal axis of the syringe body. During a fill operation or a fluid replenishment cycle, for example, a motor/actuator assembly of device 200 may drive a plunger within the syringe in sleeve 216A in one direction to draw fluid from a reservoir coupled to holder 202A into the syringe. During an injection cycle, the motor/actuator assembly of device 200 may drive the plunger within this syringe in the opposite direction to expel fluid. In one embodiment, device 200 contains two distinct motor/actuator assemblies, such that one assembly drives the syringe within sleeve 216A while another drives the syringe within sleeve 216B. However, embodiments having a single motor/actuator assembly capable of moving a plunger within both sleeves 216A, 216B are also contemplated. These motor/actuator assemblies are part of injector head 201, and may be individually controlled or monitored by the one or more processors included within injector head 201.

Input fluid tubing couples the syringes within sleeves 216A and 216B to the fluid reservoirs, according to one embodiment. In some embodiments, one or both syringes may be dual-port syringes (such as the dual-port syringe shown in FIG. 3, having separate inlet and outlet ports). In such embodiments, a first syringe port (e.g., the syringe inlet port) allows input tubing to provide fluid coupling between the syringe and a corresponding fluid reservoir, while a second syringe port (e.g., the syringe outlet port) allows output tubing to provide fluid coupling between the syringe and an output (patient) line through assemblies 218A and/or 218B.

Front-end assembly 218A is associated with sleeve 216A, and front-end assembly 218B is associated with sleeve 216B. Output tubing from the syringe in sleeve 216A runs through assembly 218A to allow for coupling to a patient line, while output tubing from the syringe in sleeve 216B runs through assembly 218B to allow for coupling to a patient line. Each of the front-end assemblies 218A and 218B may include a door, or cover, which may be opened and closed by the operator. For example, the operator may open the door in order to position or load tubing, and may close the door when tubing has been properly loaded. In some embodiments, closing of the door may assist the operator in properly positioning or "seating" the tubing in assemblies 218A and 218B. In one embodiment, a door may be made of a transparent or translucent material, such that the operator may see through the door and inside the contents of the assembly 218A or 218B, even when the door is closed, for example.

In various embodiments, either or both of the front-end assemblies 218A and 218B may include an air detector and/or valve components. Air detectors may be disposed near fluid tubing (e.g., input or output tubing), for example, to detect air bubbles or air columns within fluid tubing that has been loaded into assemblies 218A and 218B. Valve components may be used, for example, to control fluid flow (e.g., to permit, isolate, restrict, or throttle fluid flow) through tubing that has been loaded into assemblies 218A and 218B. For example, the valve components may comprise one or more pinch valves disposed along a fluid tubing path of assemblies 218A and/or 218B. When pinch valves are so used in certain embodiments, the pinch valves may be adapted to operate in one of two states: either (1) to pinch the fluid tubing shut (or closed) to isolate or prevent fluid flow in a first state, or (2) to allow the fluid tubing to stay open to permit fluid flow in a second state. Various different forms and types of valves (other than pinch valves) may also be used within assemblies 218A and 218B to control fluid flow through input and/or output tubing, as would be apparent to one of ordinary skill in the art with the benefit of these teachings. In addition, various different forms of air detectors (e.g., ultrasonic, optical) may be used, as well.

In one embodiment, the input and output tubing that is coupled to the syringe in sleeve 216A runs through front-end assembly 218A, and the input and output tubing that is coupled to the syringe in sleeve 216B runs through front-end assembly 218B. In this embodiment, each assembly 218A and 218B contains a first pinch valve and a first air detector coupled to the input tubing for the respective syringe, and further contains a second pinch valve and a second air detector coupled to the output tubing for the respective syringe. These components are more clearly shown in FIG. 2D and will be discussed in more detail below.

Figure 2B:
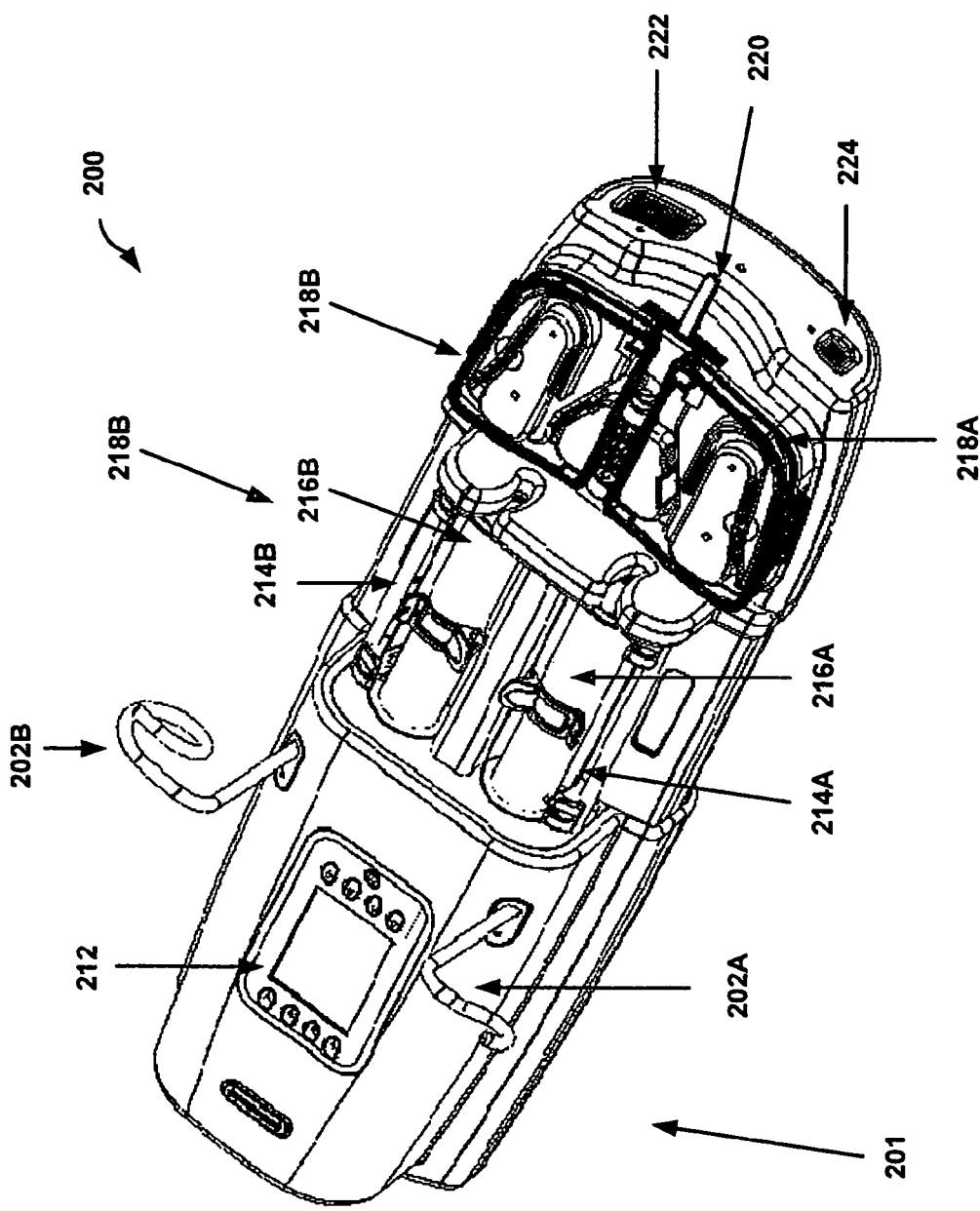
Figure 2C:
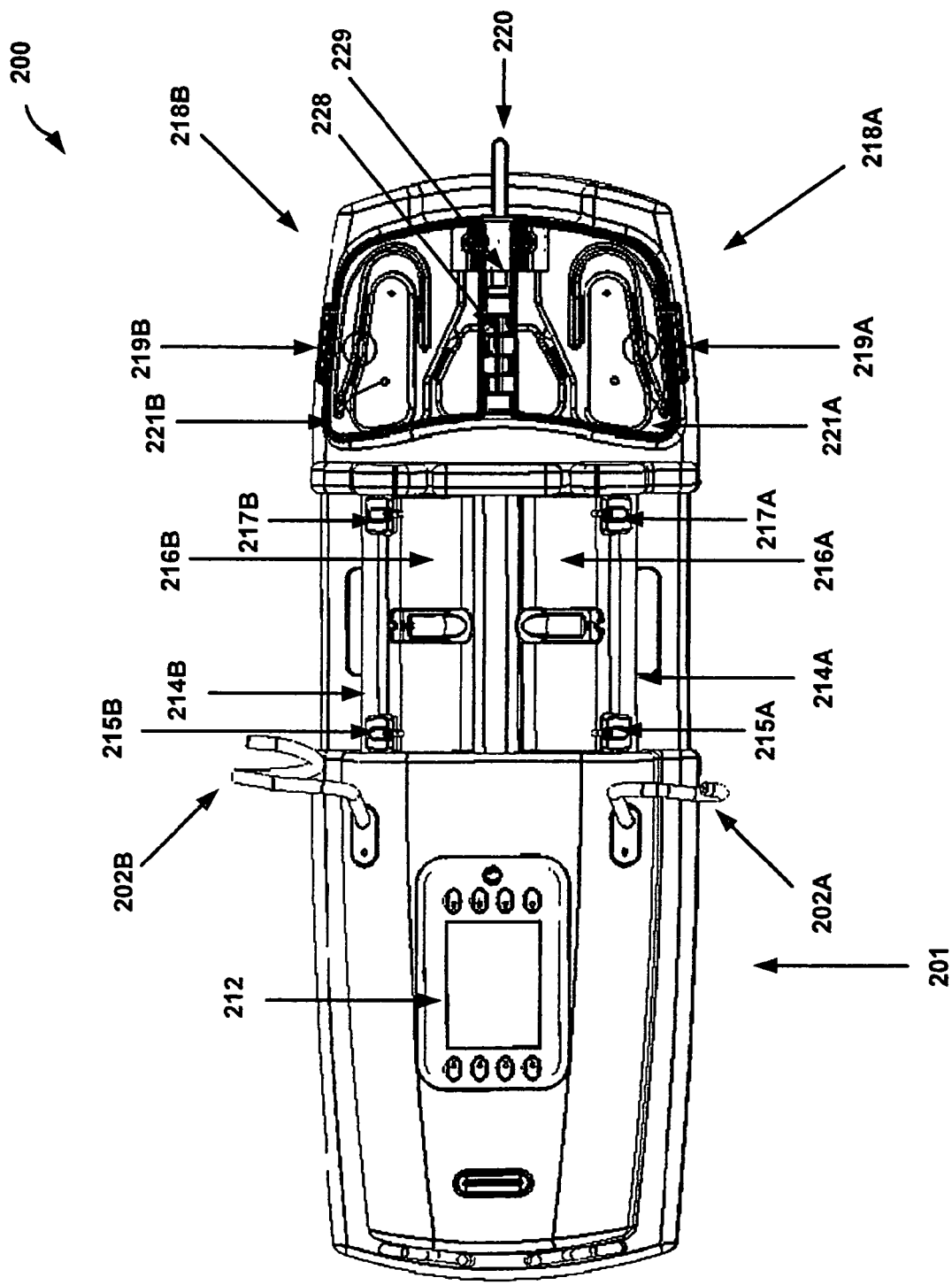
Figure 4:
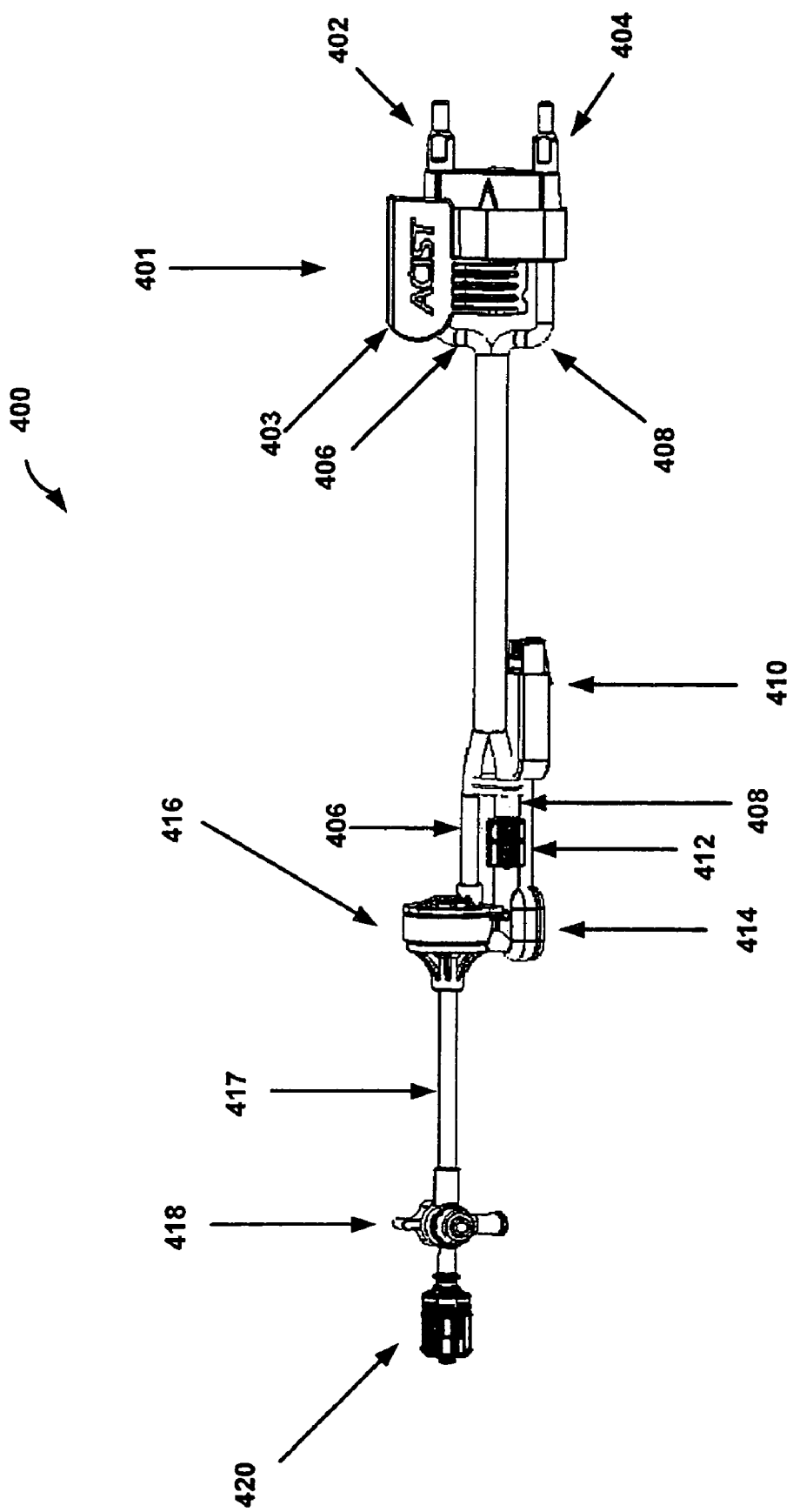
FIG. 4 is a perspective diagram of a patient line that may be used with a powered medical fluid injection device to form a portion of a flow path, according to one embodiment.

The output tubing from syringes within sleeves 216A and 216B run through front-end assemblies 218A and 218B, respectively, and are then coupled to a patient line (or patient kit, or patient tubing kit, not shown in FIG. 2A). The patient line is a single-use fluid line, according to one embodiment, which is intended to be used for a single patient procedure. A patient line may be connected to and disconnected from the output tubing coming from the front-end assemblies 218A and 218B. In some embodiments, the patient line may be connected to the output tubing by using a connection guide rod 220, as shown in FIGS. 2A-2C. For example, the patient line may include a coupling assembly adapted to align with and slide over guide rod 220 in order to facilitate coupling with the output tubing from one (or both) of the syringes. In one embodiment, the patient line includes two tubing elements adapted to be fluidly coupled to the output tubing from both of the syringes in sleeves 216A and 216B. For example, the coupling assembly, when properly positioned over guide rod 220, may cause the tubing elements of the patient line to properly align with the output tubing, and thereby facilitate fluid coupling. An example of a patient line according to such an embodiment is shown in FIG. 4 and will be discussed in more detail below.

In one embodiment, a medical fluid injection device, such as device 200, may include a plurality of pressurizing units, including three or more pressurizing units. Each of these pressurizing units may be included within a separate sleeve during operation. In some cases, multiple pressurizing units may contain the same type of fluid. For example, a first pressurizing unit may contain contrast media, a second pressurizing unit may contain a diluent (e.g., saline), and a third pressurizing unit may contain contrast media. In this scenario, the third pressurizing unit may comprise a backup, or secondary, source of contrast media. In this example, the first and third pressurizing units may both be coupled to a common front-end assembly, such as a front-end assembly similar to 218A or 218B.

FIG. 2B is another perspective diagram of the device 200 shown in FIG. 2A. In FIG. 2B, certain aspects of sleeves 216A and 216B, along with front-end assemblies 218A and 218B, can be more clearly seen. Although the doors of assemblies 218A and 218B are closed in the example of FIG. 2B, they are depicted as being made of a semi-transparent material, such that the interior pinch valve and air detector components may be more clearly seen. FIG. 2B also shows connection ports 222 and 224. In one embodiment, a pressure transducer connector (such as one coupled to connector 410 of the patient line shown in FIG. 4), may be connected to connection port 224. The pressure transducer connector is operatively coupled to a pressure transducer, which measures patient hemodynamic signals on the patient line. By coupling a signal from a pressure transducer to connection port 224, device 200 is capable of utilizing and processing hemodynamic pressure signals of a patient that are detected in the patient line.

Device 200 also includes connection port 222, which may be connected to a hand-control device (not shown). In one embodiment, the hand-control device is a disposable component that may be used by the operator for a single patient procedure. The hand-control device may control the operation of one or both of the pressurizing units (e.g., syringes) in sleeves 216A and 216B. For example, the operator may push a button or otherwise interact with the hand-control device to cause a motor/actuator assembly to inject fluid from the syringe in sleeve 216A, and may push another button or otherwise interact with the hand-control device to cause a motor/actuator assembly to inject fluid from the syringe in sleeve 216B. Thus, if the syringe in sleeve 216A contains contrast media, and the syringe in sleeve 216B contains a diluent, the operator may push one button on the hand-control device to inject contrast into the patient line, and may push another button to inject saline. In one embodiment, the hand-control device contains variable-rate functionality, such that the harder the operator pushes on a button or actuates a component, the greater the flow rate of injected fluid from the syringe in sleeve 216A or 216B.

FIG. 2C is another perspective diagram of device 200. FIG. 2C shows a top view of device 200, according to one embodiment. Connectors 215A, 215B, 217A, and 217B are more clearly shown in FIG. 2C. Connectors 215A and 217A couple sleeve 216A to rod 214A. In one embodiment, connectors 215A and 217A are coupled and attached to sleeve 216A, and are releasably coupled to rod 214A. The operator may rotate sleeve 216A about an axis defined by rod 214A to load and unload sleeve 216A. FIG. 2C shows sleeve 216A in an example loaded position, wherein fluid may be drawn into or expelled from the syringe contained within sleeve 216A. The operator may rotate sleeve 216A about the axis of rod 214A and into an unloaded position, at which point the operator may also pull on sleeve 216A to release connectors 215A and 217A from rod 214A. The operator may wish to do so, for example, to replace sleeve 216A with a new sleeve, or to clean sleeve 216A. The operator may use connectors 215A and 217A to re-attach sleeve 216A onto rod 214A. (In a similar fashion, connectors 215B and 217B couple sleeve 216B to rod 214B.)

FIG. 2C also shows doors 221A and 221B on front-end assemblies 218A and 218B, respectively. As noted above, in one embodiment, each of assemblies 218A and 218B include a moveable door 221A and 221B, respectively. Door 221A covers assembly 218A, and door 221B covers assembly 218B. In the embodiment of FIG. 2C, doors 221A and 221B are made of a transparent, or semi-transparent, material, such that an operator may see the contents of assemblies 218A and 218B (which are shown in more detail in FIG. 2D). Door 221A includes a handle 219A, and door 221B includes a handle 219B. The operator may utilize handles 219A and 219B to open and close doors 221A and 221B, respectively. Doors 221A and 221B are coupled to one or more hinges 228, which allow doors 221A and 221B to be opened and closed.

Also shown in FIG. 2C is a pivot pin 229. Pivot pin 229 is inserted through hinges 228, according to one embodiment, to securely allow doors 221A and 221B to be freely opened and closed by an operator. Doors 221A and 221B pivot about an axis that runs through pivot pin 229.

In one embodiment, pivot pin 229 is screwed into place. Pivot pin 229 may also be removed by an operator. For example, the operator may unscrew pivot pin 229 and remove it from front-end assemblies 218A and 218B. After pivot pin 229 has been removed, doors 221A and 221B may also be removed from assemblies 218A and 218B. For example, the operator may choose to remove doors 221A and 221B if the operator wishes to clean or replace doors 221A and 221B.

Figure 2D:
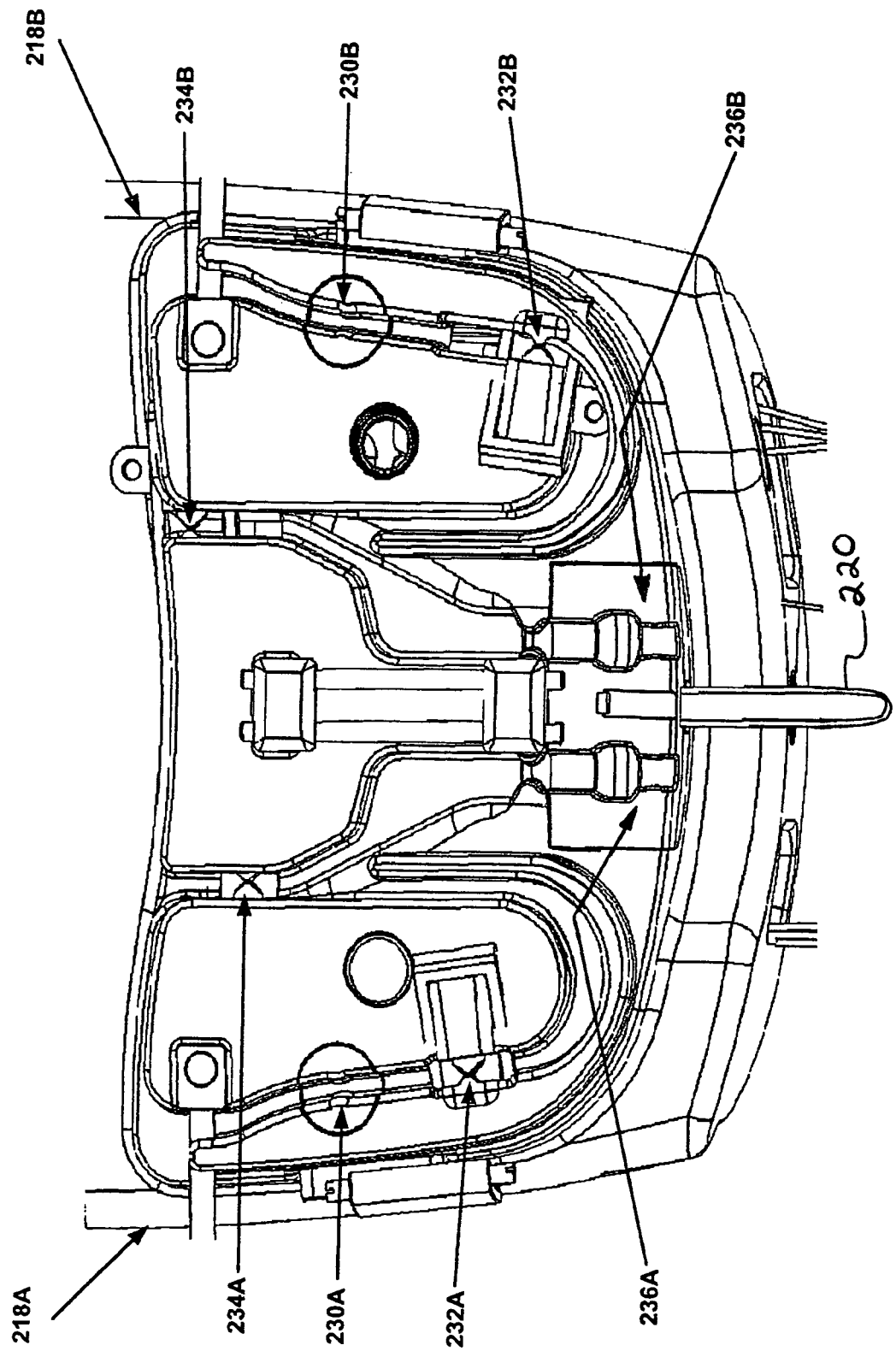

FIG. 2D is a perspective view of front-end assemblies 218A and 218B shown in more detail, according to one embodiment. Although doors 221A and 221B are not shown in FIG. 2D, they are made of a transparent, or semi-transparent, material, such that the contents of assemblies 218A and 218B may be more clearly seen by an operator, even when doors 221A and 221B are closed.

Front-end assembly 218A includes a first air detector 230A, a first pinch valve 232A, a second pinch valve 234A, and a second air detector 236A. Input tubing from a reservoir on holder 202A runs through air detector 230A and pinch valve 232A and into a syringe in sleeve 216A via a first syringe port (e.g., the syringe inlet port), according to one embodiment. Output tubing coupled to a second syringe port of the syringe (e.g., the syringe outlet port) in sleeve 216A runs through pinch valve 234A and air detector 236A and is then coupled to an external patient line, or kit (such as the one shown in FIG. 4). Air detector 230A is used to detect air bubbles or columns within the input tubing, and air detector 236A is used to detect air bubbles or columns within the output tubing. Air detectors 230A and 236A may comprise acoustic-based, optical-based, or other forms of air detectors. If either or both air detectors detect the presence of air (or some measurable threshold quantity of air) in the input and/or output tubing, the air detectors may be adapted to generate and send a signal (or signals) to injector head 201 of device 200. One or more processors of injector head 201 may process these received signals. Injector head 201 may provide a warning message or alert to the operator via control panel 212, such that the operator may take appropriate action. In some embodiments, injector head 201 may also be adapted to automatically pause or terminate any injection of fluid if air has been detected in the input and/or output tubing by controlling (e.g., stopping) operation of the motor/actuator assembly driving the syringe.

Pinch valve 232A controls the flow of fluid from a fluid reservoir, through input tubing, and into the syringe in sleeve 216A. Injector head 201 controls the operation of pinch valve 232A. When injector head 201 causes pinch valve 232A to open, fluid is permitted to flow from the reservoir connected to holder 202A and into the syringe. When pinch valve 232A is closed, no fluid flow is permitted within the input tubing. For example, when injector head 201 is supplying the syringe with fluid, it may open pinch valve 232A to allow fluid flow into the syringe via the input tubing. During such operation, injector head 201 may also close pinch valve 234A, to prohibit any fluid flow from the syringe via the output tubing. The plunger within the syringe may be moved in a first direction (e.g., the syringe may be retracted by the motor/actuator assembly) to supply fluid to the syringe (e.g., from the reservoir via the input tubing). When a fluid injection occurs, the motor/actuator assembly will move the plunger within the syringe in a second, opposite direction (e.g., the syringe may be advanced by the motor/actuator assembly). Injector head 201 may close pinch valve 232A during an injection procedure to prohibit fluid flow in the input tubing. However, injector head 201 may open pinch valve 234A to allow fluid flow in the output tubing during such an injection procedure. In such fashion, injector head 201 utilizes pinch valves 232A and 234A to control fluid flow in the input and output tubing during various operations (e.g., replenishment and injection operations).

In one embodiment, pinch valves 232A and 234A are solenoid-based pinch valves. In other embodiments, other forms of pinch valves 232A and 234A may be used, such as pneumatic-based valves or motor driven valves. In one embodiment, pinch valves 232A and 234A have default states in the closed position. Thus, when device 200 is neither supplying fluid into nor injecting fluid from the syringe in sleeve 216A, both pinch valves 232A and 234A are closed. Pinch valves 232A and 234A may then be opened by device 200 when energy is actively applied to pinch valves 232A and/or 234A. When no energy is applied to pinch valves 232A and/or 234A, they return to a default, closed position. Thus, if there are any power failures to device 200, valves 232A and 234A will return to a closed position. This functionality, when implemented, may operate as a safety feature of device 200.

Similarly, front-end assembly 218B includes a first air detector 230B, a first pinch valve 232B, a second pinch valve 234B, and a second air detector 236B. Input tubing from a reservoir connected to holder 202B runs through air detector 230B and pinch valve 232B and into a first syringe port of the syringe in sleeve 216B. Output tubing coupled to a second syringe port of the syringe runs through pinch valve 234B and air detector 236B, and may then be coupled to a patient line. The components within device 218B function similarly to those contained within device 218A as described above, according to one embodiment.

In one embodiment, device 200 of FIGS. 2A-2D is capable of initiating fluid replenishment cycles for the syringes in sleeves 216A and/or 216B during different operational states of device 200. In this embodiment, injector head 201 may obtain operational state information for the device, such as, for example, the type of operational state information described with reference to FIGS. 1A-1B. Injector head 201 then is capable of using the operational state information to determine whether it will permit a fluid replenishment operation for one or both of the syringes. If a fluid replenishment operation is permitted for one of these syringes, injector head 201 then initiates a fluid replenishment operation with a determined amount of medical fluid. The operational state information includes information other than a fluid delivery volume for a subsequent injection procedure, according to one embodiment, such that device 200 need not necessarily know an amount of fluid that is to be injected from the syringe in sleeve 216A or 216B for a patient injection procedure in order to determine whether or not to allow and initiate a fluid replenishment operation. This may provide a more effective and efficient way by which to supply the syringes with fluid.

For example, injector head 201 may obtain operational state information at a given point in time to determine that device 200 is injecting fluid from the syringe in sleeve 216A, but is not injecting fluid from the syringe in sleeve 216B. Given this operational state information, injector head 201 may then be able to determine that it can supply the syringe in sleeve 216B with fluid, if necessary, given that this syringe is not currently being used to inject fluid. Injector head 201 may first check to see if this syringe is already full, such as by checking additional operational state information or by making a calculation. If the syringe is already full, injector head 201 need not initiate a fluid replenishment operation, since it determines that a supply amount would essentially be equal to zero. If, however, the syringe is not full to capacity, injector head 201 may supply the syringe in sleeve 216B with a determined amount of fluid. For example, injector head 201 may cause the syringe to be completely filled to capacity. Or, injector head 201 may otherwise use operational state information to determine an amount of fluid to use during the fluid replenishment operation.

Injector head 201 may determine whether the syringe in sleeve 216B is already full using a number of different approaches. For example, in one scenario, injector head 201 may use operational state information to determine how much fluid remains in the syringe. In another scenario, injector head 201 may calculate an amount of remaining fluid based upon an amount of fluid that has been injected from the syringe in prior injection procedures, which may also be obtained from operational state information of device 200. Operational state information includes current and past state information about device 200, including operational information, injection parameters used, error messages, alert conditions, and any other related information.

Using another example, injector head 201 may also gather operational state information indicating that neither of the syringes in sleeves 216A or 216B is being used to inject fluid at a given time. This may be the case when an operator is using control panel 212 to set up injection parameters for one or more subsequent procedures to be performed. In this case, injector head 201 may initiate a fluid replenishment operation for both of the syringes.

When injector head 201 is supplying the syringe in sleeve 216A or 216B with fluid, it continually monitors the state of device 200, according to one embodiment. If the state of device 200 changes, injector head 201 may pause or abort a fluid replenishment operation that is taking place. For example, if device 200 is automatically supplying the syringe in sleeve 216A with fluid, but detects that the operator now wants to initiate an injection procedure using fluid from this syringe, injector head 201 will stop the fluid replenishment operation and initiate an injection operation. During any of these operations, injector head 201 may utilize one or more of its processors to perform certain operations.

In one embodiment, a fluid replenishment operation may be permitted if at least a determined amount of time has elapsed since a prior injection of medical fluid from one of the pressurizing units (e.g., syringes) in sleeve 216A or 216B. For example, when a syringe delivers fluid to a catheter in a patient, a clinician may inject intermittent, frequent "puffs" of contrast media from device 200 during placement of the catheter within the patient. In this example, it may sometimes be beneficial to avoid, or prohibit, replenishment operations in between these "puff" injections. Thus, a fluid replenishment operation may, in some cases, only be permitted if a pre-determined amount of time (e.g., typically about 3 seconds, but potentially up to 10 seconds or more) has elapsed since a prior injection, or "puff," of contrast media. In some cases, a fluid replenishment operation may be permitted if a fluid volume in the syringe has decreased at least a determined amount since a prior replenishment operation was performed.

Table 1 below shows examples of a number of different states of operation of device 200 during which one or more fluid replenishment operations of the syringes in sleeves 216A and 216B may be initiated. From the examples shown in Table 1, it is assumed that the syringe in sleeve 216A is used for injecting contrast media and that the syringe in sleeve 216B is used for injecting saline, which is a diluent. Additional states and/or operations to those listed may also be possible.

TABLE 1

| STATE OF INJECTION DEVICE 200 | FLUID REPLENISH OPERATION |
|---|---|
| Contrast media purge from syringe in sleeve 216A | Supply saline to syringe in sleeve 216B |
| Saline purge from syringe in sleeve 216B | Supply contrast media to syringe in sleeve 216A |
| Contrast media injection from syringe in sleeve 216A | Supply saline to syringe in sleeve 216B |
| Saline injection (or KVO cycle) from syringe in sleeve 216B | Supply contrast media to syringe in sleeve 216A |
| Injection parameter entry/change by operator on control panel 212 | Supply contrast media to syringe in sleeve 216A and/or supply saline to syringe in sleeve 216B |
| Standby mode for device 200 | Supply contrast media to syringe in sleeve 216A and/or supply saline to syringe in sleeve 216B |
| Contrast media reservoir change by operator (such as by replacing reservoir on holder 202A) | Supply saline to syringe in sleeve 216B |
| Saline reservoir change by operator (such as by replacing reservoir on holder 202B) | Supply contrast media to syringe in sleeve 216A |

In the examples of Table 1, purge operations from the syringes in sleeves 216A and/or 216B occur when device 200 is being primed, or prepared, for patient use. Thus, during purge operations, device 200 is not yet connected to a patient. Conversely, during injection operations from the syringes, fluids are injected into a patient. Device 200 may also be used for "Keep Vessel Open" (KVO) operations. A KVO operation occurs when small amounts of diluent are repeatedly or continuously injected. Also in reference to Table 1, device 200 may be in standby mode when neither syringe is being used to inject fluid. For example, device 200 may enter standby mode after a patient case has been finished, and before the operator has entered parameters or otherwise configured the device using panel 212 for a new case. In one embodiment, the examples shown in Table 1 are based upon an assumption that only one of the contrast media or diluent is injected at a time.

In some cases, during an automatic fluid replenishment operation, a user or operator may intervene by interacting with the control panel, such as control panel 102 (FIG. 1A) or control panel 212. For instance, an operator may choose to terminate a fluid replenishment operation, or may choose to modify one or more fluid supply parameters.

FIG. 3 is a perspective diagram of an example syringe 301 that may be used within device 200, according to one embodiment. Syringe 301 may be loaded in either sleeve 216A or 216B. If syringe 301 is loaded into sleeve 216A, it may be coupled to a fluid reservoir connected to holder 202A (FIG. 2A), and may further be coupled to a patient line (FIG. 4).

Syringe 301 is a dual-port syringe in the example shown in FIG. 3. Syringe inlet port 300 is coupled to input tubing 308, and syringe outlet port 302 is coupled to output tubing 304. Input tubing 308 is coupled to a connector 310, which may be connected to a fluid reservoir in holder 202A, assuming syringe 301 is loaded into sleeve 216A. For example, if connector 310 is a spike, the spike may be inserted into a bottle of medical fluid connected to holder 202A. Output tubing 304 is coupled to a connector 306, which is adapted to couple output tubing 304 to a separate patient line. In one embodiment, connector 306 is a Luer-type connector.

Fluid is drawn from the fluid reservoir into inlet port 300 of syringe 301 via input tubing 308. Fluid is expelled from outlet port 302 of syringe 301 into output tubing 304. Input tubing 308 may run through air detector 230A and pinch valve 232A (FIG. 2D) of front-end assembly 218A, which was described above, while output tubing 304 may run through pinch valve 234A and air detector 236A. In one embodiment, syringe 301, along with input tubing 308, connector 310, output tubing 304, and connector 306, are disposable, multi-use components. That is, these components may be used in with device 200 over multiple uses or patient procedures before they are disconnected from device 200 and disposed of. In another embodiment, these components are disposable, single-use components, meaning that they are disposed of after a single patient procedure.

In one embodiment, syringe 301 may also be used in device 100 (FIG. 1A). When used in device 100, connector 310 would be connected to a fluid reservoir on holder 110, and output tubing 304 would run through patient manifold sensor 114.

FIG. 4 is a perspective diagram of a patient line 400 (sometimes referred to as a patient tubing kit or patient kit) that may be used with the injection device 200 shown in FIGS. 2A-2D, according to one embodiment. Patient line 400 includes a coupling assembly 401, a valve 416, a stopcock 418, and a connector 420. Patient line 400 is used to provide fluid coupling from one or more pressurizing units of device 200 to a patient catheter that is used to deliver medical fluid to a patient.

Coupling assembly 401 includes a first connector 402 and a second connector 404. When assembly 401 is used to couple patient line 400 to device 200, connector 402 is fluidly coupled with a connector for output tubing from one of the syringes in sleeves 216A or 216B, while connector 404 is fluidly coupled with a connector for output tubing from the other syringe. For example, connector 402 may be connected to connector 306 (FIG. 3), which is coupled to output tubing 304 for the syringe in sleeve 216A. Patient line 400 is a disposable kit, in one embodiment, such that connectors 402 and 404 may be connected to and removed from tubing connectors, such as connector 306, by the operator. In one embodiment, patient line 400 is a single-use disposable kit, such that it is connected to device 200 for one patient use, and then subsequently disconnected and discarded.

Assembly 401 may by coupled to device 200 by sliding it over guide rod 220 of device 200 and locking it into place, according to one embodiment. Lever 403 may be used to lock and unlock assembly 401 when it has been coupled to device 200 via guide rod 220. Lever 403 may be moved into a first position to lock assembly 401 on guide rod 220, and may be moved into a second position to unlock assembly 401. For example, an operator may pull up on lever 403 to lock assembly 401, such that it may be secured and prepared for use during an injection procedure. Pulling up on lever 403 may, for example, cause connectors 402 and 404 to become fully seated, or positively coupled, with the corresponding tubing connectors of the respective syringes, such as tubing connector 306. After the injection procedure has been completed, the operator may push down on level 403 to unlock assembly 401, such that it may be removed from guide rod 220, allowing patient line 400 to be discarded.

Connection guide rod 220 may, in some cases, help to maintain the sterility of connectors 402 and 404 by aligning these connectors, during insertion, to prevent contact with non-sterile items. As described above, when coupling assembly 401 is locked into place by actuation of lever 403 by an operator, connectors 402 and 404 may be thereby pulled into the injector head and into fluid communication with one or more fluid connectors 306 of the one or more corresponding syringes 301. In some embodiments, actuation of lever of 403 of coupling assembly 401 may also result in positioning of connectors 402 and 404 near corresponding air column detection sensors in the injector head of device 200, for example.

Within patient line 400, connector 402 is operatively coupled to tubing 406, and connector 404 is operatively coupled to tubing 408. In one embodiment, connector 402 is coupled to the syringe in sleeve 216A, which contains contrast media, while connector 404 is coupled to the syringe in sleeve 216B, which contains a diluent such as saline. Thus, in this embodiment, contrast media is injected via tubing 406 of patient line 400, while diluent is injected via tubing 408. Tubing 406 and 408 are coupled to valve 416, which, in one embodiment, comprises an elastomeric-type valve that allows fluid flow from only one of tubing 406 and 408 to output tubing 417. In one embodiment, valve 416 comprises a one-way valve that allows fluid flow only in the direction towards output tubing 417.

As is shown in FIG. 4, tubing 408 is coupled to check valve 412 and transducer 414. In one embodiment, check valve 412 comprises a bi-directional check valve. In one embodiment, transducer 414 comprises a pressure transducer that is capable of measuring hemodynamic signals (e.g., blood pressure) of a patient when patient line 400 is coupled to a catheter that has been inserted into the patient. Transducer connector 410 may be coupled to device 200, such as by way of port 224 (FIG. 2B). When coupled to device 200 in this manner, hemodynamic signals generated by transducer 414 may be provided to a processor within device 200 and processed and/or displayed, or such signals may be routed from device 200 to another device for processing and/or display.

Output tubing 417 is coupled to stopcock 418 and to connector 420 shown in FIG. 4. Stopcock 418 may be manually manipulated by the operator to control fluid flow, and may also be connected to other external devices, such as a syringe or an external pressure transducer. Connector 420 is used to connect patient line 400 to a catheter that may deliver fluid to a patient. In one embodiment, connector 420 comprises a Luer-type connector, a connector known in the art.

In one embodiment, patient line 400 may also be used with device 100 shown in FIG. 1A. When used with device 100, transducer connector 410 may be coupled to a mating port within device 100 (not shown), such that a processor of device 100 may process hemodynamic signals generated by transducer 414. Coupling assembly 401 may also be coupled to device 100 in this embodiment. Patient line 400 may be coupled to a manifold valve that is coupled to patient manifold sensor 114, such that connection port 402 may be coupled to tubing from the syringe, while connection port 404 may be coupled to tubing running through pump 106. In this embodiment, output tubing 417 may also be coupled to, or run through, air detector 116 of device 100.

Despite the use of known procedures to remove or purge air from a medical fluid injection system, it has been noted that air may remain present (or may become present over time) in the fluid flow path in sufficient quantities to be detected by air detection sensors. In some cases, the presence of even very small air bubbles may result in an alarm condition and/or a termination of an injection procedure (either manually or automatically). Upon thorough investigation, the inventors have discovered that small air or gas bubbles (e.g., "micro bubbles," typically on the order of 1 to 5 micro liters in volume) may become trapped in fluid system components, typically as a result of making various fluid connections. Such micro bubbles may form and/or be compressed at or near the fluid connections between various portions of the fluid injection system and/or at discontinuities in the fluid flow path. Such small air bubbles may remain trapped or hidden during the course of normal injection system operations (including initial system set-up, flushing, and/or purging procedures). However, over time, these air bubbles may migrate and/or expand into other portions of the fluid injection system where they could potentially become injected with the next (or a subsequent) injection to a patient.

In addition to the potential patient safety concern posed by the presence of air bubbles in a fluid injection system, there may be considerable inconvenience associated with any alarms and/or automatic shutdowns caused by the detection of these small air bubbles. The detection of air may also result in additional time spent performing any additional purging or flushing operations needed to clear the air bubbles and the associated air detection alarm condition. Furthermore, the relatively slow migration of "trapped" air bubbles into the fluid flow path could give rise to successive alarms and/or shutdowns over an extended period of time. This could give rise to frustration and anxiety by a user of the medical fluid injection system, as well as diminished confidence in the performance of the system. It has thus become desirable to find a way to quickly and efficiently remove air that may remain trapped in portions of a medical fluid injection system (even after typical purging and flushing procedures), particularly in the areas at or near fluid connections.

Figure 5A:
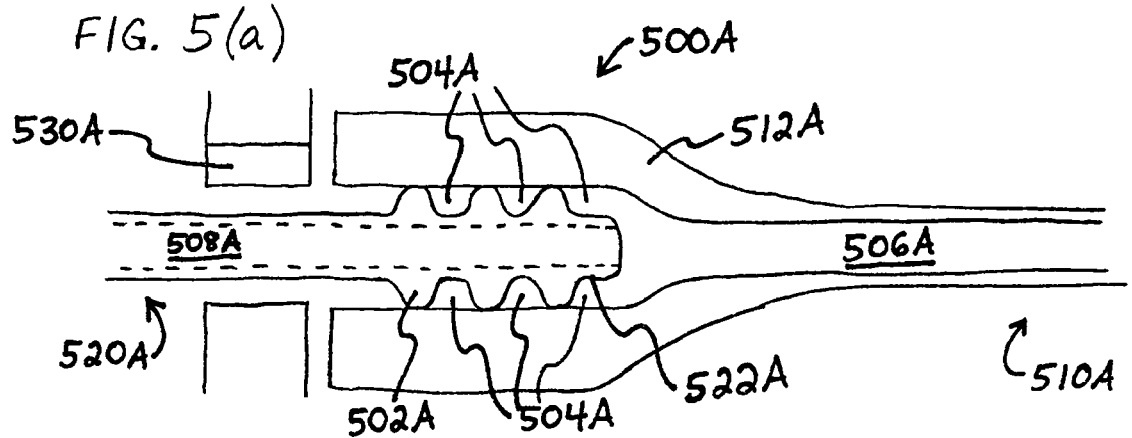
FIGS. 5(a)-5(d) are cross-sectional side views of exemplary fluid connectors which may be used with a powered medical fluid injection device to establish a fluid flow path, according to certain embodiments.

FIGS. 5(a)-5(d) show several examples of fluid connectors that might be used to form fluid connections or fluid couplings in a medical fluid injection system. For example, FIG. 5(a) shows a fluid connection between two fluid conduits. Fluid conduit 510A may be referred to as an upstream fluid conduit, and fluid conduit 520A may be referred to as a downstream fluid conduit, for example, although a fluid could flow in either direction. (During an injection, fluid would typically flow in a direction from the upstream fluid conduit toward the downstream fluid conduit.) The fluid connector 500A may further comprise a "male" fitting 522A associated with fluid conduit 520A, and a "female" fitting 512A associated with fluid conduit 510A. The fluid connector 500A may further comprise a sealing component 502A (part of male fitting 522A, as shown in FIG. 5(a)), which may be adapted to be compressed when the two connector fittings 512A, 522A are operably engaged in order to form a fluid seal. Sealing component 502A in FIG. 5(a) may, for example, comprise one or more fins or ribs projecting radially outward from fitting 522A to form a seal between the outside of male fitting 522A and the inside of female fitting 512A. Sealing component 502A may be formed of an elastomeric material, according to some embodiments. In such a fluid seal arrangement, one or more pockets 504A may be formed in the process of engaging the connector fittings 512A, 522A, and in the course of forming the fluid seal, small amounts of air may become compressed and/or trapped in one or more of such pockets 504A. Over time, small air bubbles at or near a fluid connector 500A (such as air trapped in pockets 504A) may migrate or expand away from pockets 504A. In some cases, trapped air bubbles may migrate past sealing component 502A into fluid path 506A, where they may subsequently be injected into flow path 508A. If an air detector is present along flow path 508A (such as ultrasonic air column detector 530A, as shown in FIG. 5(a)), small air bubbles (on the order of 1 to 5 micro liters) may be detected by air detector 530A and trigger an air detection condition, which may then result in an alarm condition and/or automatic termination of any injection procedure in progress.

Figure 5B:
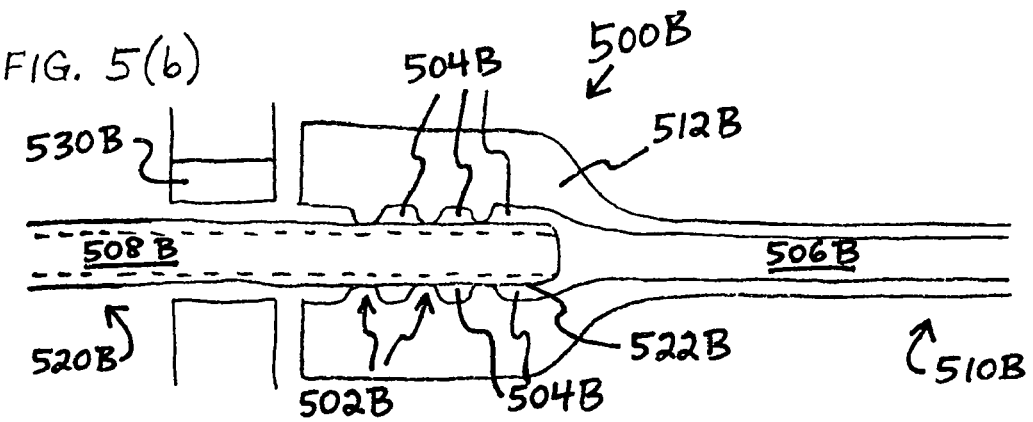

Similarly, FIG. 5(b) shows a fluid connection between two fluid conduits. Fluid conduit 510B may be referred to as an upstream fluid conduit, and fluid conduit 520B may be referred to as a downstream fluid conduit, for example, although a fluid could flow in either direction. (During an injection, fluid would typically flow in a direction from the upstream fluid conduit toward the downstream fluid conduit.) The fluid connector 500B may comprise a "male" fitting 522B associated with fluid conduit 520B, and a "female" fitting 512B associated with fluid conduit 510B. The fluid connector 500B may further comprise a sealing component 502B (part of female fitting 512B, as shown in FIG. 5(b)), which may be adapted to be compressed when the two connector fittings 512B, 522B are operably engaged in order to form a fluid seal. Sealing component 502B in FIG. 5(b) may, for example, comprise one or more fins or ribs projecting radially inward from fitting 512B to form a seal between the inside of female fitting 512B and the outside of male fitting 522B. Sealing component 502B may be formed of an elastomeric material, according to some embodiments. In such a fluid seal arrangement, one or more pockets 504B may be formed in the process of engaging the connector fittings 512B, 522B, and in the course of forming the fluid seal, small amounts of air may become compressed and/or trapped in one or more of such pockets 504B. Over time, small air bubbles at or near a fluid connector 500B (such as air trapped in pockets 504B) may migrate or expand away from pockets 504B. In some cases, trapped air bubbles may migrate past sealing component 502B into fluid path 506B, where they may subsequently be injected into flow path 508B. If an air detector is present along flow path 508B (such as air column detector 530B, as shown in FIG. 5(b)), small air bubbles (on the order of 1 to 5 micro liters) may be detected by air detector 530B and trigger an air detection condition, which may then result in an alarm condition and/or automatic termination of any injection procedure in progress.

Figure 5C:
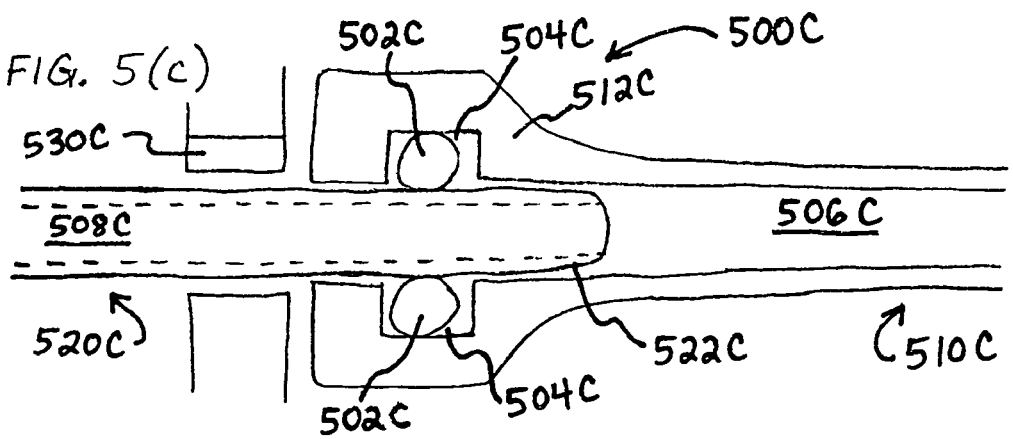
Figure 5D:
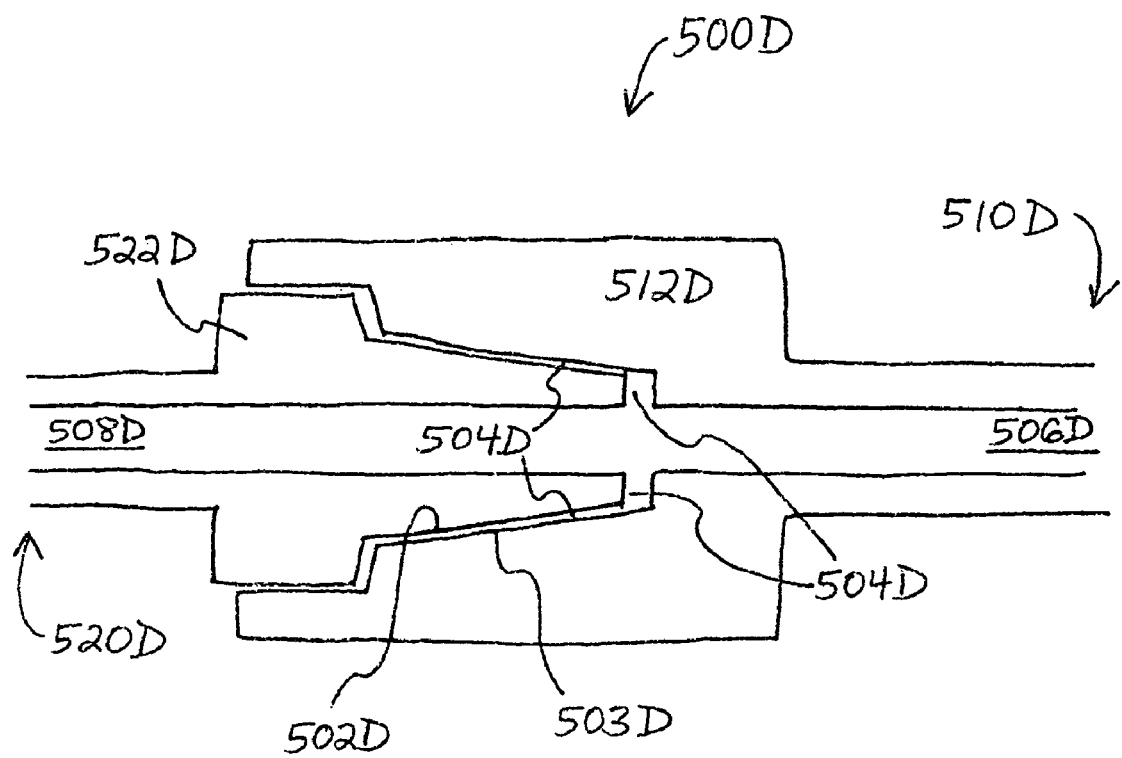

Similarly, FIG. 5(c) shows a fluid connection between two fluid conduits. Fluid conduit 510C may be referred to as an upstream fluid conduit, and fluid conduit 520C may be referred to as a downstream fluid conduit, for example, although a fluid could flow in either direction. (During an injection, fluid would typically flow in a direction from the upstream fluid conduit toward the downstream fluid conduit.) The fluid connector 500C may comprise a "male" fitting 522C associated with fluid conduit 520C, and a "female" fitting 512C associated with fluid conduit 510C. The fluid connector 500C may further comprise a sealing component 502C (e.g., an O-ring which may be a portion of fitting 512C, as shown in FIG. 5(*c*)), or which may be a portion of fitting 522C, which may be adapted to be compressed when the two connector fittings 512C, 522C are operably engaged in order to form a fluid seal. Sealing component 502C may be formed of an elastomeric material, according to some embodiments. In such a fluid seal arrangement, one or more pockets 504C may be formed in the process of engaging the connector fittings 512C, 522C, and in the course of forming the fluid seal, small amounts of air may become compressed and/or trapped in one or more of such pockets 504C. Over time, small air bubbles at or near a fluid connector 500C (such as air trapped in pockets 504C) may migrate or expand away from pockets 504C. In some cases, trapped air bubbles may migrate into fluid path 506C, where they may subsequently be injected into flow path 508C. If an air detector is present along flow path 508C (such as air column detector 530C, as shown in FIG. 5(*c*)), small air bubbles (on the order of 1 to 5 micro liters) may be detected by air detector 530C and trigger an air detection condition, which may then result in an alarm condition and/or automatic termination of any injection procedure in progress.

FIG. 5(*d*) shows a fluid connection comprising a "Luer" fitting between two fluid conduits. Luer fittings are fluid fittings used for making relatively leak-free connections between a male taper fitting and its tapered female mating counterpart. Interference, friction, and/or compression between the two tapered portions is employed to make the seal. Fluid conduit 510D may be referred to as an upstream fluid conduit, and fluid conduit 520D may be referred to as a downstream fluid conduit, for example, although a fluid could flow in either direction. (During an injection, fluid would typically flow in a direction from the upstream fluid conduit toward the downstream fluid conduit.) The fluid connector 500D may comprise a "male" Luer fitting 522D associated with fluid conduit 520D, and a "female" Luer fitting 512D associated with fluid conduit 510D. The male Luer fitting 522D may comprise a tapered portion 502D, and the female Luer fitting 512D may comprise a corresponding tapered portion 503D, such that an outer surface of tapered portion 502D forms a compression seal with an inner surface of tapered portion 503D when the two connector fittings 512D and 522D are operably engaged in order to form a fluid seal. In such a fluid seal arrangement, one or more pockets 504D may be formed in the process of engaging the connector fittings 512D and 522D and in the course of forming the fluid seal, small amounts of air may become compressed and/or trapped in one or more of such pockets 504D. Over time, small air bubbles at or near a fluid connector 500D (such as air trapped in pockets 504D) may migrate or expand away from pockets 504D. In some cases, trapped air bubbles may migrate into fluid path 506D, where they may subsequently be injected into flow path 508D. If an air detector is present along flow path 508D (such as an air column detector), small air bubbles (on the order of 1 to 5 micro liters) may be detected by the air detector and trigger an air detection condition, which may then result in an alarm condition and/or automatic termination of any injection procedure in progress.

In an embodiment of the invention, a method of removing air from a flow path of a medical fluid injection system may include the steps shown in the flow diagram of FIG. 6. For example, in step 610, a first amount of a medical fluid (e.g., saline solution, contrast media) is delivered to a flow path of a medical fluid injection system. Such a step may assume, for example, that a relevant flow path has already been established for the medical fluid injection system. The flow path may comprise a downstream fluid portion and an upstream fluid portion in fluid communication via a fluid connector disposed therebetween, the upstream fluid portion also being in fluid communication with a pressurizing unit (e.g., a syringe, or a pump) of the medical fluid injection system. The first amount of medical fluid may be delivered by actuating the pressurizing unit of the medical fluid injection system to cause the medical fluid to move from the pressurizing unit through the upstream fluid portion and into the downstream fluid portion. The first amount of medical fluid to be delivered may be an amount sufficient to displace a certain volume of the flow path, or to substantially fill the flow path, for example.

In step 620, fluid isolation is provided along the flow path between the fluid connector and the pressurizing unit. In some embodiments, fluid isolation may be provided, for example, by closing a valve (such as a pinch valve) in the upstream fluid portion of the flow path. In step 630, a vacuum is created in the pressurizing unit. This may be done in embodiments where, for example, the pressurizing unit comprises a syringe, by retracting a plunger within a chamber of the syringe (e.g., by moving the plunger in a direction away from the point of fluid isolation, or rearward). The vacuum condition created results in fluid pressure being lower upstream of the point of fluid isolation than it is downstream of the point of fluid isolation.

In step 640 of FIG. 6, fluid communication from the pressurizing unit to the downstream fluid portion is re-established (e.g., the fluid isolation provided in step 620 is removed). This may be done, for example, by opening a valve (such as a pinch valve) in the upstream fluid portion of the flow path. Typically, this is done by re-opening the same valve that was closed to provide fluid isolation in step 620. Re-establishing fluid communication exposes the fluid connector and the downstream fluid portion to the vacuum condition created in step 630. Any air bubbles thereby exposed to the vacuum will expand in size and tend to move or migrate in a direction toward the pressurizing unit. It may be advantageous, in some embodiments, to have the air bubbles migrate into the pressurizing unit (e.g., syringe). For example, air bubbles that migrate back into certain types of pressurizing units (for example, the syringe designs shown in FIGS. 3 and 7(*a*)-(*b*), having an inlet port disposed near a top portion and an outlet port disposed near a bottom portion of the pressurizing unit) will tend to float to the top of the syringe, where they are not likely to be subsequently pushed back into the flow path (e.g., upon subsequent delivery of fluid from the pressurizing unit to the flow path). This feature or aspect may be further enhanced in some particularly preferred embodiments of the invention by having the pressurizing unit angled slightly upward (e.g., angled so that the end of the pressurizing unit with the outlet port is angled upward, anywhere from about 1 to 20 degrees from horizontal, and preferably from about 8 to 15 degrees from horizontal). The up angle of the pressurizing unit should cause air bubbles that migrate into the pressurizing unit to float up to the topmost and forwardmost portion of the pressurizing unit.

In step 650, a second amount of the medical fluid is delivered to the flow path. The medical fluid may again be delivered by actuating the pressurizing unit of the medical fluid injection system to cause the medical fluid to move from the pressurizing unit through the upstream fluid portion and into the downstream fluid portion. The second amount of medical fluid may, for example, be an amount sufficient to move any previously trapped air bubbles (e.g., air bubbles drawn out of areas or pockets near the fluid connector) through the flow path (e.g., past a certain portion of the downstream fluid portion, or past the end of the downstream fluid portion). In some embodiments, an optional step may include a test for the presence of air. Such a step may be performed following the delivery of the second amount of the medical fluid to the flow path. If air is detected, step 650 is repeated. If no air is detected, the method of removing air from the flow path of a medical fluid injection system is considered complete.

Figure 7A:
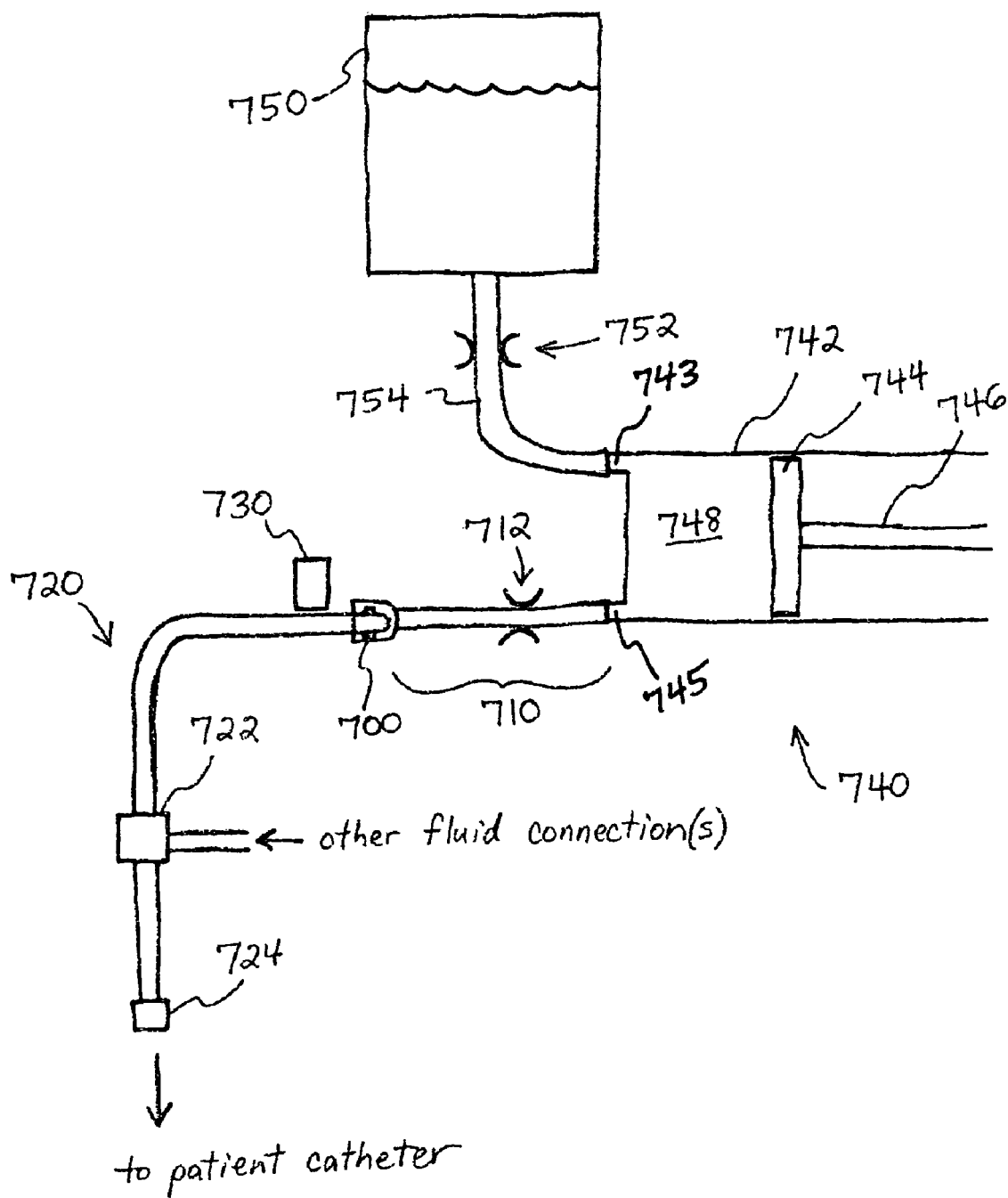
FIG. 7(a) is a schematic diagram of a powered medical fluid injection system that may employ the method illustrated in FIG. 6, according to one embodiment.

FIG. 7(*a*) illustrates an exemplary medical fluid injection system in which air may be removed by a method according to certain embodiments of the invention. Use of the method described herein is not limited to the particular medical fluid injection system shown in FIG. 7(*a*); with the benefit of these teachings, one of ordinary skill in the art would be able to adapt the various methods described for use with other fluid injection systems. Typically, pressurizing unit 740 is filled with a medical fluid (e.g., contrast agent or saline) prior to performing an injection. The medical fluid may be supplied to pressurizing unit 740 from a medical fluid reservoir 750 via fluid supply tubing 754, according to some embodiments. For example, in a medical fluid injection system in which the pressurizing unit 740 comprises a syringe 742, a plunger 744 may be retracted or withdrawn (e.g., moved to the right in FIG. 7(*a*)) within the syringe 742 to draw fluid from fluid reservoir 750, through fluid supply tubing 754, which is coupled to syringe 742 via syringe inlet 743, and into chamber 748 of syringe 742. The plunger 744 may be coupled via a ram 746 to a motorized drive mechanism (not shown) of the medical fluid injection system, which is adapted to enable linear motion (both forward and rearward) of the plunger 744 within syringe 742, according to some embodiments. Valve 752 (e.g., pinch valve) may be opened to allow filling of syringe 742 via syringe inlet 743, and may be closed during fluid injection procedures.

Once pressurizing unit 740 is at least partially filled with a medical fluid, valve 752 may be closed so that the air removal method described above with reference to FIG. 6 may be performed. A first amount of fluid is delivered to a flow path by moving fluid from pressurizing unit 740 (e.g., from a chamber 748 of a syringe 742), through upstream fluid portion 710, through fluid connector 700, and into downstream fluid portion 720. A valve, such as valve 712 (e.g., a pinch valve, check valve, or other type of fluid valve), in proximity to or associated with upstream fluid portion 710 must be open (e.g., at least partially open) to allow the first amount of fluid to be delivered to the flow path. In the exemplary injection system shown in FIG. 7(*a*), the first amount of fluid is delivered by advancing plunger 744 within syringe 742 to cause the first amount of fluid to move from chamber 748 into and through the flow path.

The first amount of fluid delivered to the flow path may be an amount chosen to displace a certain volume of the flow path, or to substantially fill the flow path. For example, the first amount of fluid may be a volume approximately equal to the volume of the flow path from the outlet 745 of syringe 742 to a certain point in the downstream fluid portion 720, such as to the location of an air detector 730, or to a multi-port valve 722, or to the end connector 724, for example. The first amount of fluid delivered provides an initial fill condition within the flow path. Next, fluid isolation is provided along the upstream fluid portion 710. This may be done in the system shown in FIG. 7(*a*) by closing valve 712. Valve 712 may be a pinch valve, or may be another type of fluid valve, for example.

Once fluid isolation is provided (e.g., valve 712 is in the closed position), a vacuum is created "upstream" of the point of fluid isolation. This may be done using the pressurizing unit 740. For example, in the system of FIG. 7(*a*), a vacuum condition may be created by retracting plunger 744 of syringe 742. (Note: This assumes that valve 752 is also in the closed position in the embodiment of FIG. 7(*a*).) A certain amount of vacuum may be desired (e.g., a drop in pressure within chamber 748 of a certain amount, or retraction of plunger 744 by a certain linear distance) before proceeding to the next step. (In preferred embodiments, the retraction of plunger 744 should correspond to a volume displacement of fluid that is less than the volume of fluid in the downstream fluid portion 720 to avoid bringing air from the end of downstream fluid portion 720 too far into the flow path.) After the desired vacuum condition is attained, fluid communication is re-established along the upstream fluid portion 710, for example, by opening valve 712. Re-establishing fluid communication exposes fluid connector 700 to the vacuum condition, which causes air bubbles that may be trapped in or around the fluid connector 700 to expand and/or migrate into the upstream fluid portion 710 and/or possibly into the syringe chamber 748. As noted above, air bubbles that migrate all the way into the syringe chamber 748 will tend to float to a top portion of the syringe chamber 748, where they will likely be prevented from re-entering the flow path on a subsequent injection (e.g., during a subsequent advancement of the syringe plunger 744).

Next, a second amount of fluid is delivered to the flow path to move the "released" air bubbles through the flow path (e.g., through the upstream fluid portion 710, and at least to a certain portion of the downstream fluid portion 720). For example, in some embodiments, the second amount of fluid delivered may be chosen to be large enough that an air bubble that has migrated back into the syringe chamber 748 is thereby moved all the way through the downstream fluid portion 720 (e.g., past the end connector 724). In other embodiments, the second amount of fluid may be chosen to move released air bubbles past some intermediate point in the downstream fluid portion 720, such as past the air detector 730, or past the multi-port valve 722. In some embodiments, an additional step may be incorporated where the delivery of the second amount of fluid is repeated following detection of an air bubble.

In some preferred embodiments of the invention, air bubbles that migrate back into the syringe chamber 748 will remain there and/or be purged through an inlet port and back into a fluid reservoir 750, for example, according to some embodiments, whereas typically, it is the air bubbles that are drawn into the upstream fluid portion 710 that will be "flushed" via the delivery of the second amount of fluid. The second amount of fluid may be selected to take into account the various scenarios described above, for example, and/or to cause air bubbles in the upstream fluid portion 710 to be flushed beyond a certain point in the flow path and/or to do so while minimizing the amount of medical fluid (e.g., contrast media) used in the process.

In some embodiments where air bubbles have migrated back into the syringe chamber 748, for example, such air bubbles may be expelled back into fluid reservoir 750 by opening valve 752, closing valve 712, and driving plunger 744 forward (e.g., advancing plunger 744) within syringe 742 to push such air bubbles from chamber 748 through tubing 754 and back into fluid reservoir 750. This advancement of the syringe plunger 744 may occur in conjunction with the advancement of plunger 744 used to deliver the second amount of fluid, described above, or it may be done as a separate step.

Figure 7B:
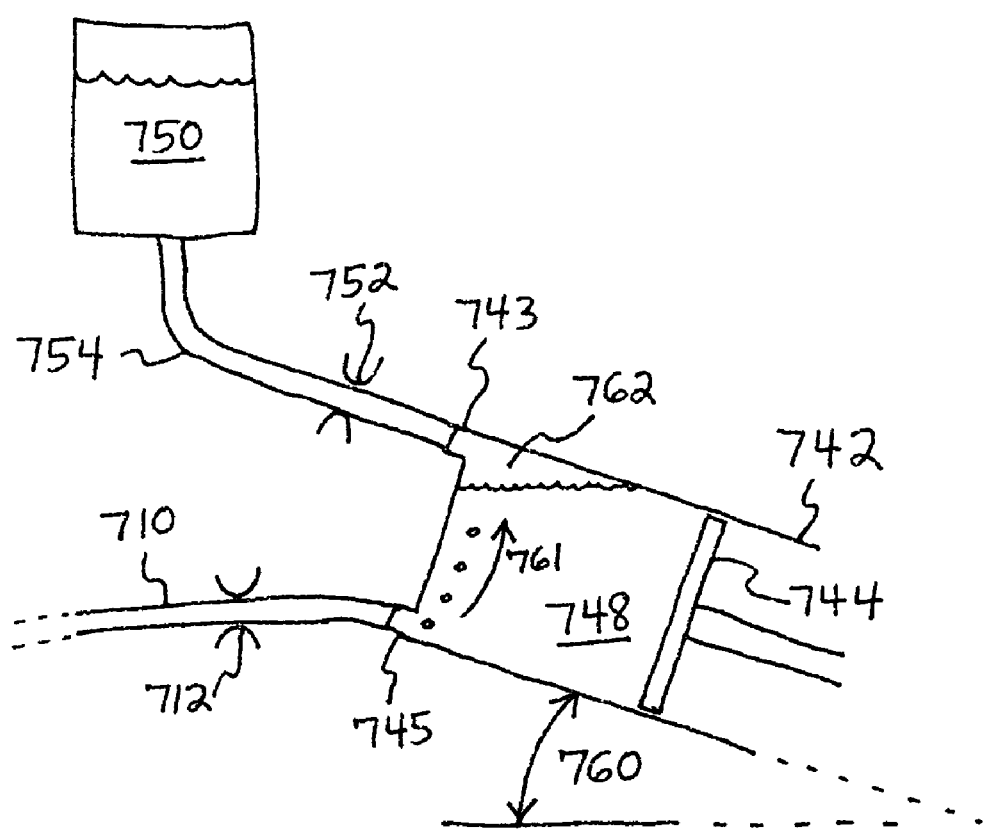
FIG. 7(b) is a schematic diagram of a powered medical fluid injection system employing a pressurizing unit disposed at an angle, according to one embodiment.

In some embodiments, it may be desirable to purge such air bubbles from the syringe chamber 748 back into the fluid reservoir 750 prior to delivering the second amount of fluid. In one embodiment, syringe 742 is maintained at an angle 760 (see FIG. 7(b)) to cause air bubbles that have migrated into syringe 742 to float upwards as indicated by the arrow 761 in FIG. 7(b) (e.g., due to the lower density of air as compared to the medical fluid) and coalesce into a single, larger air bubble near a portion 762 of syringe 742. In further preferred embodiments, angle 760 may be an "up" angle as depicted in FIG. 7(b), which will tend to cause the coalesced air bubble in portion 762 to be in a top, forwardmost portion of syringe 742 (e.g., near inlet 743), as is also shown in FIG. 7(b). Such an arrangement should facilitate the purging of air bubbles from the syringe 742 back into the fluid reservoir 750, according to some embodiments.

Figure 8:
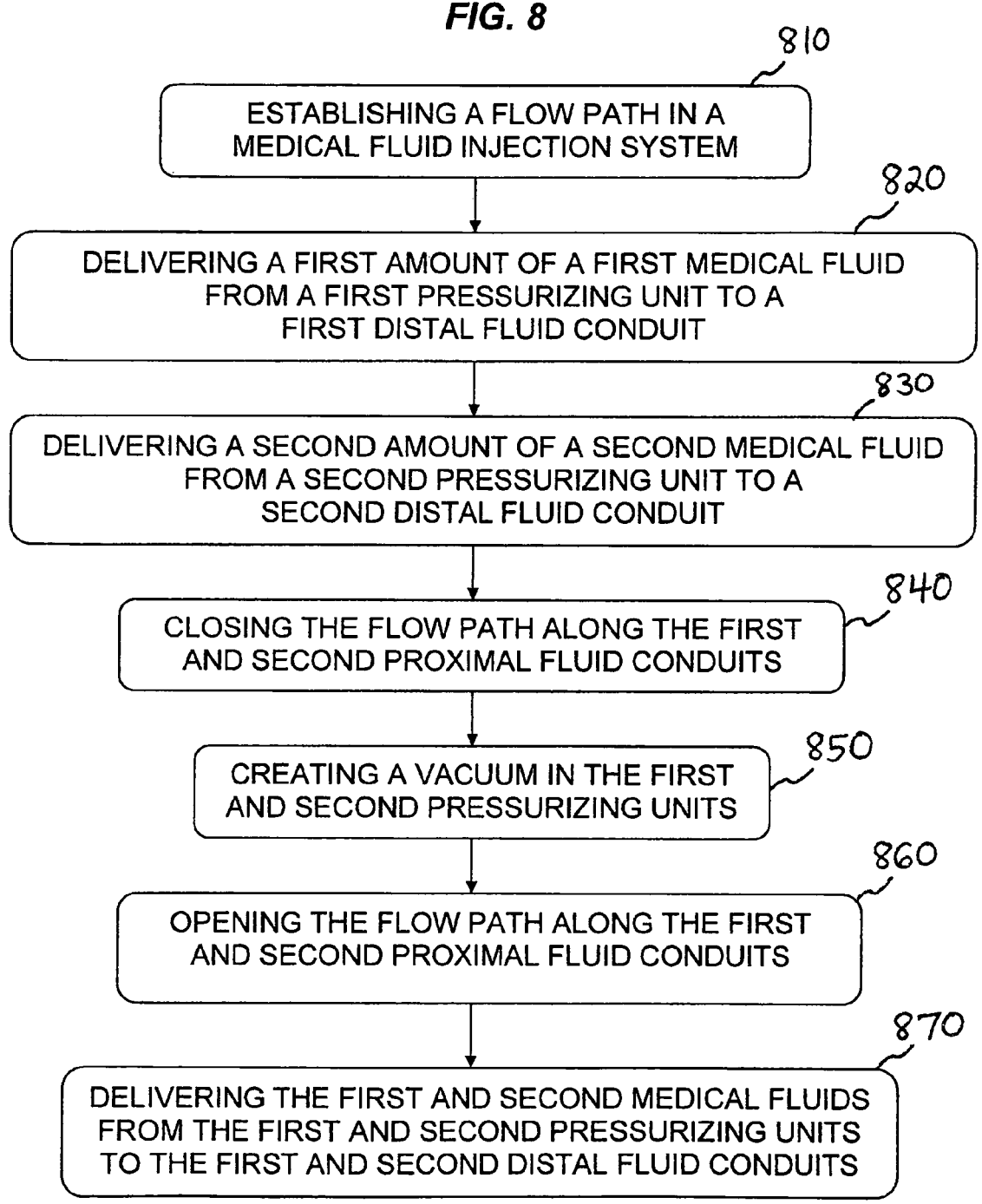
FIG. 8 is a flow diagram of a method that may be performed by a powered medical fluid injection device to remove air from a flow path, according to one embodiment.

In another embodiment of the invention, a method of removing air from a flow path of a medical fluid injection system having two or more pressurizing units may include the steps shown in the flow diagram of FIG. 8. For example, in step 810, a flow path is established in a medical fluid injection system. Establishing the flow path may comprise making one or more fluid connections that allow or enable fluid to be delivered from a pressurizing unit to a patient catheter, for example. The flow path may comprise one or more downstream fluid portions (distal fluid conduits) and one or more upstream fluid portions (proximal fluid conduits) in fluid communication via one or more fluid connectors disposed therebetween. The upstream fluid portions are also placed in fluid communication with pressurizing units of the medical fluid injection system. In some embodiments, a pressurizing unit (e.g., a syringe) may come pre-packaged or pre-assembled with the upstream fluid portion fluidly coupled to an outlet of the syringe, for example, as part of a sterile kit. In such an embodiment, establishing a flow path might include positioning the pre-assembled syringe and upstream fluid portion to facilitate making a fluid connection to a downstream fluid portion, for example. Establishing a flow path might include connecting a downstream fluid portion to an upstream fluid portion via a fluid connector such as those described above with respect to FIGS. 5(a) thru 5(d).

In step 820, a first amount of a first medical fluid (e.g., contrast media, saline, etc.) is delivered from a first pressurizing unit, through at least a portion of the established flow path, to a first distal fluid conduit (or first downstream fluid portion). The first medical fluid may be delivered by using the first pressurizing unit to force fluid from the pressurizing unit through the upstream fluid portion and into the downstream fluid portion. The first amount of medical fluid to be delivered may be an amount sufficient to displace a certain volume of the flow path, or to substantially fill the flow path, for example. In step 830, a second amount of a second medical fluid (e.g., saline, contrast media, etc.) is delivered from a second pressurizing unit, through at least a portion of the established flow path, to a second distal fluid conduit (or second downstream fluid portion).

In step 840, the flow path is closed along the upstream fluid portions (or the proximal fluid conduits), for example, between each fluid connector and the corresponding pressurizing unit. Fluid isolation may be provided, for example, by closing a valve (such as a pinch valve) disposed along each of the upstream fluid portions of the flow path. In step 850, a vacuum is created in the first and second pressurizing units. This may be done, for example, in embodiments where the pressurizing unit comprises a syringe, by retracting a plunger in a chamber of the syringe (e.g., by moving the plunger in a direction away from the point of fluid isolation, or rearward).

In step 860 of FIG. 8, fluid communication from the pressurizing unit to the downstream fluid portion is re-established (e.g., the fluid isolation provided in step 840 is removed) by opening the flow path along the first and second proximal fluid conduits (or upstream fluid portions). This may be done, for example, by opening a valve (such as a pinch valve) in the upstream fluid portion of the flow path. Re-establishing fluid communication will expose the fluid connector and the downstream fluid portion to the vacuum condition created in step 850. Any air bubbles thereby exposed to the vacuum will expand in size and tend to move in a direction toward the pressurizing units. In step 870, the first and second medical fluids are delivered to the flow path. The medical fluids may be delivered by using the respective pressurizing units to force fluid from each pressurizing unit through the upstream fluid portions and into the downstream fluid portions. The amounts of the first and second medical fluids delivered may, for example, be sufficient to move any previously trapped air bubbles (e.g., air bubbles drawn out of areas or pockets near the fluid connectors) through the flow path (e.g., past a certain portion of the downstream fluid portions, or past the end of the downstream fluid portions, or past a multi-port connector adapted to receive fluid from two or more downstream fluid portions). In some embodiments, delivery of the amounts of the first and second medical fluids may be repeated, for example, following the detection of an air bubble.

Figure 9:
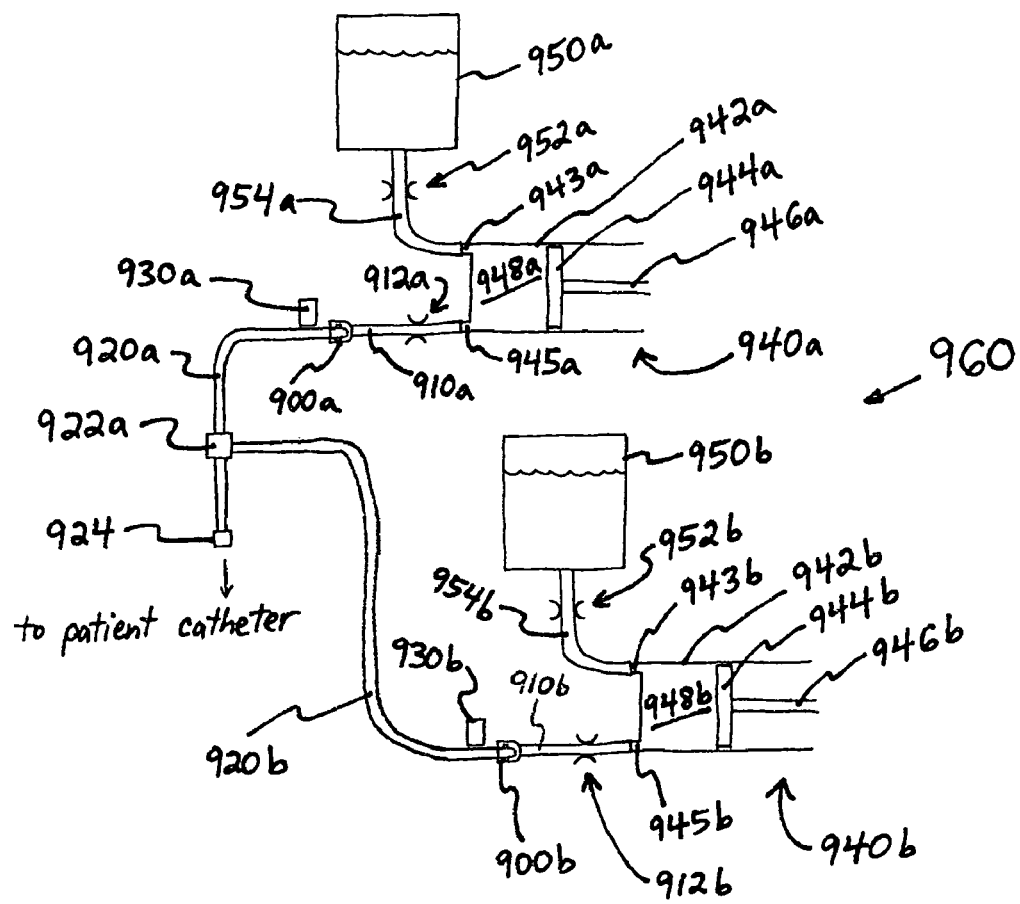
FIG. 9 is a schematic diagram of a powered medical fluid injection system that may employ the method illustrated in FIG. 8, according to one embodiment.

FIG. 9 illustrates an exemplary medical fluid injection system 960 in which air may be removed by a method according to certain embodiments of the invention. Use of the method described herein is not limited to the particular medical fluid injection system shown in FIG. 9; with the benefit of these teachings, one of ordinary skill in the art would be able to adapt the various methods described herein for use with other fluid injection systems. Typically, pressurizing units 940a, 940b are filled with a medical fluid (e.g., contrast media and/or saline) prior to performing an injection. (Pre-filled pressurizing units are known in the art, and their use with various embodiments of the invention is also contemplated.) For example, a first medical fluid (e.g., a contrast media) may be supplied to a first pressurizing unit 940a from a medical fluid reservoir 950a via fluid supply tubing 954a, according to some embodiments. For example, in a medical fluid injection system in which the pressurizing unit 940a comprises a syringe 942a, a plunger 944a may be retracted or withdrawn (e.g., moved to the right in FIG. 9) within the syringe 942a to draw fluid from fluid reservoir 950a, through fluid supply tubing 954a, and into chamber 948a of syringe 942a. The plunger 944a may be coupled via a ram 946a to a motorized drive mechanism (not shown) of the medical fluid injection system, which is adapted to enable linear motion (both forward and rearward) of the plunger 944a within syringe 942a, according to some embodiments. Valve 952a (e.g., a pinch valve) may be opened to allow filling of syringe 942a via syringe inlet 943a, and may be closed during fluid injection procedures.

Similarly, a second medical fluid (e.g., saline) may be supplied to a second pressurizing unit 940b from a medical fluid reservoir 950b via fluid supply tubing 954b, according to some embodiments. For example, in a medical fluid injection system in which the pressurizing unit 940b comprises a syringe 942b, a plunger 944b may be retracted or withdrawn (e.g., moved to the right in FIG. 9) within the syringe 942b to draw fluid from fluid reservoir 950b, through fluid supply tubing 954b, and into chamber 948b of syringe 942b. The plunger 944b may be coupled via a ram 946b to a motorized drive mechanism (not shown) of the medical fluid injection system, which is adapted to enable linear motion (both forward and rearward) of the plunger 944b within syringe 942b, according to some embodiments. Valve 952b (e.g., a pinch valve) may be opened to allow filling of syringe 942b via syringe inlet 943b, and may be closed during fluid injection procedures.

Once pressurizing units 940a, 940b are at least partially filled with medical fluid, valves 952a, 952b may be closed so that an air removal method (such as the steps described above with reference to FIG. 8) may be performed. FIG. 9 shows a portion of an exemplary medical fluid injection system 960 having two pressurizing units 940a, 940b. A flow path is established in the medical fluid injection system. Establishing the flow path may comprise making one or more fluid connections that allow or enable fluid to be delivered from the pressurizing units 940a, 940b to a patient catheter (not shown), for example, via end connector 924. The flow path may comprise one or more downstream fluid portions 920a, 920b and one or more upstream fluid portions 910a, 910b in fluid communication via one or more fluid connectors 900a, 900b disposed between the respective upstream and downstream fluid portions. The upstream fluid portions 910a, 910b are also placed in fluid communication with pressurizing units 940a, 940b of the medical fluid injection system. In some embodiments, a pressurizing unit (e.g., a syringe) may come pre-packaged or pre-assembled with the upstream fluid portion fluidly coupled to an outlet of the syringe, for example, as part of a sterile kit. In such an embodiment, establishing a flow path might include positioning the pre-assembled syringes and upstream fluid portions to facilitate making fluid connections to the respective downstream fluid portions, for example.

When forming fluid connections between the one or more downstream fluid portions 920a, 920b and the one or more upstream fluid portions 910a, 910b (e.g., to establish a fluid flow path), fluid connectors 900a, 900b may be used that are similar to those shown and described with respect to FIGS. 5(a)-5(d). As described above, the formation of these fluid connections may allow or cause air to become trapped near the fluid connectors 900a, 900b, and this trapped air may migrate into the flow path over time.

A first amount of a first medical fluid (e.g., contrast media) is delivered to the flow path in FIG. 9, for example, by moving fluid from pressurizing unit 940a, through upstream fluid portion 910a, through fluid connector 900a, and into a first distal fluid conduit (downstream fluid portion 920a). Valve 912a (e.g., a pinch valve or other type of fluid valve) in upstream fluid portion 910a must be at least partially open to allow the first amount of the first medical fluid to be delivered to the flow path. In the exemplary injection system shown in FIG. 9, the first amount of the first medical fluid may be delivered by advancing plunger 944a within syringe 942a to cause the first amount of the first medical fluid to move from the syringe and into and through the flow path. The first amount of the first medical fluid may be an amount chosen to displace a certain volume of the flow path, or to substantially fill the flow path. For example, the first amount of the first medical fluid may be a volume approximately equal to the volume of the flow path from the outlet 945a of the syringe 942a to a certain point in the downstream fluid portion 920a, such as to the location of an air detector 930a, or to a multi-port valve 922a, or to the end connector 924, for example.

Likewise, a second amount of a second medical fluid (e.g., saline) is delivered to the flow path in FIG. 9, for example, by moving fluid from pressurizing unit 940b, through upstream fluid portion 910b, through fluid connector 900b, and into a second distal fluid conduit (downstream fluid portion 920b). Valve 912b (e.g., a pinch valve or other type of fluid valve) in upstream fluid portion 910b must be at least partially open to allow the second amount of the second medical fluid to be delivered to the flow path. In the exemplary injection system shown in FIG. 9, the second amount of the second medical fluid may be delivered by advancing plunger 944b within syringe 942b to cause the second amount of the second medical fluid to move from the syringe and into and through the flow path. The second amount of the second medical fluid may be an amount chosen to displace a certain volume of the flow path, or to substantially fill the flow path. For example, the second amount of the second medical fluid may be a volume approximately equal to the volume of the flow path from the outlet 945b of the syringe 942b to a certain point in the downstream fluid portion 920b, such as to the location of an air detector 930b, or to a multi-port valve 922a, or to the end connector 924, for example. Delivering the first amount of the first medical fluid and delivering the second amount of the second medical fluid provides an initial fill condition within the flow path.

Fluid isolation is provided along the proximal fluid conduits (upstream fluid portions 910a, 910b) by closing the flow paths between each fluid connector 900a, 900b and its corresponding pressurizing unit 940a, 940b. This may be done in the system shown in FIG. 9 by closing valves 912a and 912b, for example. Valves 912a, 912b may be pinch valves, or may be another type of fluid valve, for example, adapted to provide fluid isolation along a length of fluid tubing.

Once the flow path is closed along the first and second proximal fluid conduits (e.g., valves 912a, 912b are closed), a vacuum is created "upstream" of each of the points of fluid isolation. This may be done, for example, by using the pressurizing units 940a, 940b. For example, in the system of FIG. 9, a vacuum condition may be created by retracting plungers 944a, 944b within each of the respective syringes 942a, 942b. (Note: This assumes that valves 952a and 952b are also in the closed position in the embodiment illustrated in FIG. 9.) A certain amount of vacuum may be desired (e.g., a drop in pressure within chambers 948a, 948b of a certain amount, or retraction of plungers 944a, 944b by a certain linear distance) before proceeding to the next step.

After the desired vacuum condition is achieved in the pressurizing units 940a, 940b, fluid communication is re-established along the upstream fluid portions 910a and 910b, for example, by opening the flow paths along the first and second proximal fluid conduits (e.g., by opening valves 912a and 912b). Re-establishing fluid communication in this manner exposes fluid connectors 900a, 900b to the vacuum condition, which causes air bubbles that may be trapped in or around the fluid connector 900a, 900b to expand and/or migrate into the upstream fluid portions 910a, 910b (and/or possibly into the syringe chambers 948a, 948b).

Additional amounts of the first and second medical fluids are then delivered to the flow path to move the "released" air bubbles through the flow path (e.g., from the syringes 940a, 940b, through the upstream fluid portions 910a, 910b, and at least to a certain portion of the downstream fluid portions 920a, 920b). For example, in some embodiments, the amounts of the first and second medical fluids delivered in this step may be chosen to be large enough so that an air bubble that has migrated back into a syringe chamber 948a, 948b is moved all the way through the fluid flow path (e.g., past the end connector 924). In other embodiments, the amounts of fluid delivered may be chosen to move any released air bubbles past some intermediate point in the downstream fluid portions 920a, 920b, such as past the air detectors 930a, 930b, or past the multi-port valve 922a.

As noted above with respect to FIG. 7(b), one or both syringes 940a and 940b of system 960 may be disposed at an angle to facilitate movement and/or coalescence of air bubbles that move into either or both of the syringes (e.g., to prevent subsequent injection of such bubbles, and/or to facilitate air bubble removal via purging of the affected syringes). For example, in some embodiments, air bubbles that have migrated back into syringe chambers 948a or 948b may be forced into fluid reservoirs 950a or 950b by opening valve 952a or 952b (as appropriate) while closing corresponding valve 912a or 912b, and driving the respective plunger 944a or 944b forward (e.g., to the left in FIG. 9) within syringe 942a or 942b to push fluid from chambers 948a or 948b into fluid reservoirs 950a or 950b.

In a particularly preferred embodiment, a method of removing air from the medical fluid injection system 960 of FIG. 9 may incorporate the following steps. Step 1: with both inlet pinch valves 952a,b initially closed, outlet pinch valves 912a,b are opened. Step 2: An amount of contrast media (e.g., 5 mL) is delivered from syringe 942a by advancing plunger 944a at a rate corresponding to about 5 mL per second to substantially fill the flow path from the proximal fluid conduit 910a through the distal fluid conduit 920a, and past multi-port valve 922a. Step 3: An amount of saline (e.g., 6 mL) is delivered from syringe 942b by advancing plunger 944b at a rate corresponding to about 5 mL per second to substantially fill the flow path from the proximal fluid conduit 910b through the distal fluid conduit 920b, and past multi-port valve 922a. Step 4: Close the outlet pinch valves 912a,b. Step 5: Retract both plungers 944a,b substantially simultaneously, to create a vacuum condition upstream of the outlet pinch valves 912a,b by displacing a volume of 2 mL in each syringe 942a,b at a rate of 2.5 mL per second. Step 6: Open the outlet pinch valves 912a,b. Step 7: Advance both plungers 944a,b, substantially simultaneously, to displace 2 mL each at a rate of 2.5 mL per second, thereby collapsing certain air bubbles. Step 8: Deliver an amount of contrast media (e.g., 6 mL) at a rate of about 8 mL per second to clear any air bubbles past the multi-port valve 922a. In certain preferred embodiments, if air bubbles are detected at the air column detect 930a during the delivery of the amount of contrast media (e.g., 6 mL), additional contrast media is delivered until the amount of contrast media (e.g., 6 mL) has been delivered without an air bubble detection. Step 9: Deliver an amount of saline (e.g., 7 mL) at a rate of about 8 mL per second to clear any air bubbles past the multi-port valve 922a. In certain preferred embodiments, if air bubbles are detected at the air column detect 930b during the delivery of the amount of saline (e.g., 7 mL), additional saline is delivered until the amount of saline (e.g., 7 mL) has been delivered. Step 10: Pause for about 0.5 seconds. Step 11: Deliver an amount of saline (e.g., 7 mL) at a rate of about 8 mL per second to clear any remaining air bubbles out through the end of the patient line (e.g., past end connector 924). Step 12: Close outlet pinch valves 912a,b. If air is detected during steps 8 through 12, some or all of steps 8 through 12 may be repeated, according to some embodiments. It should be noted that the volumes and flow rates above are provided as illustrative examples, and that these could vary without departing from the scope of the invention as claimed.

The particular fluid amounts and flow rates, as well as the order and timing of steps described above may be well suited to the particular systems and components depicted herein, and may yield a desired result (e.g., removal of air) in a relatively short period of time, while minimizing the amount of expensive contrast media used. Further, such a sequence of steps may be well-suited to be performed in an automated fashion by the medical fluid injection system. For example, as noted earlier, the injector head may typically have an internal processor adapted to carry out instructions. Such instructions would likely be stored on a computer-readable medium such that, when the internal processor of the injector head reads the instructions from the computer-readable medium, the steps could be carried out automatically. Thus, a single button press (or other suitable user-actuation mechanism) could trigger the system to perform the air removal method substantially as described above.

In certain alternate embodiments of the invention, it may be desirable to modify the methods described above. One such alternate embodiment adds the step of "back-filling" fluid after drawing the vacuum, and before re-establishing fluid communication along the flow path. For example, in embodiments where the vacuum is created upstream of the fluid isolation by retracting the syringe plunger a certain distance "X," fluid would be delivered (or back-filled) by advancing the syringe plunger some distance less than "X." Thus, some amount of vacuum would still be present, but the back-fill step may result in some air bubbles (e.g., air bubbles that migrate into the syringe chamber) being compressed (e.g., back into solution). In a preferred alternate embodiment, the back-fill step may follow a "larger-than-normal" vacuum creation in the preceding step. For example, if the vacuum is normally created by retracting a syringe plunger a linear distance of 3 cm in the syringe chamber, one might employ the back-fill step following a plunger retraction of 5 cm, wherein the back-fill step could comprise advancement of a syringe plunger a certain distance "Y." The distance "Y" could, for example, yield the same net retraction (e.g., a 2 cm advancement following a 5 cm retraction would result in the same 3 cm net plunger retraction), or it could result in some different endpoint (e.g., a different amount of net plunger retraction and/or vacuum created). In further alternate embodiments, the vacuum creation and back-fill steps may be performed multiple times, for example, to provide greater assurance that air bubbles have been removed from the flow path.

In further alternate embodiments, the method of removing air may further comprise closing a downstream fluid valve (e.g., a pinch valve located downstream of a fluid connection, or a stopcock at the end of a patient line, such as stopcock 418, shown in FIG. 4), then creating a vacuum along the fluid path (e.g., along the entire patient line 400 of FIG. 4). This could be performed as an added step, either before or after the normal steps of creating the vacuum and re-establishing fluid communication. For example, in one possible alternate embodiment of the invention, patient line 400 could be filled with medical fluids (e.g., both contrast and saline lines) past the stopcock 418. Stopcock 418 could then be closed. A first vacuum could then be created on portions of the fluid flow path, or on the entire flow path (e.g., by retracting one or both plungers in embodiments with two fluid syringes) to force air bubbles to be released from any trapped locations along the entire patient line 400, for example. Fluid isolation could then next be applied along the upstream flow path(s), in embodiments where this is possible (e.g., where there are pinch valves in an upstream portion of the flow path). Optionally, a further vacuum could next be drawn by further retraction of one or both syringes. Re-establishing fluid communication might next be performed to cause further release and/or migration of released air bubbles. Advancement of one or both syringe plungers to move any released air bubbles could be performed next, followed by opening of the stopcock 418 to "flush" out any such remaining released air bubbles.

Figure 10:
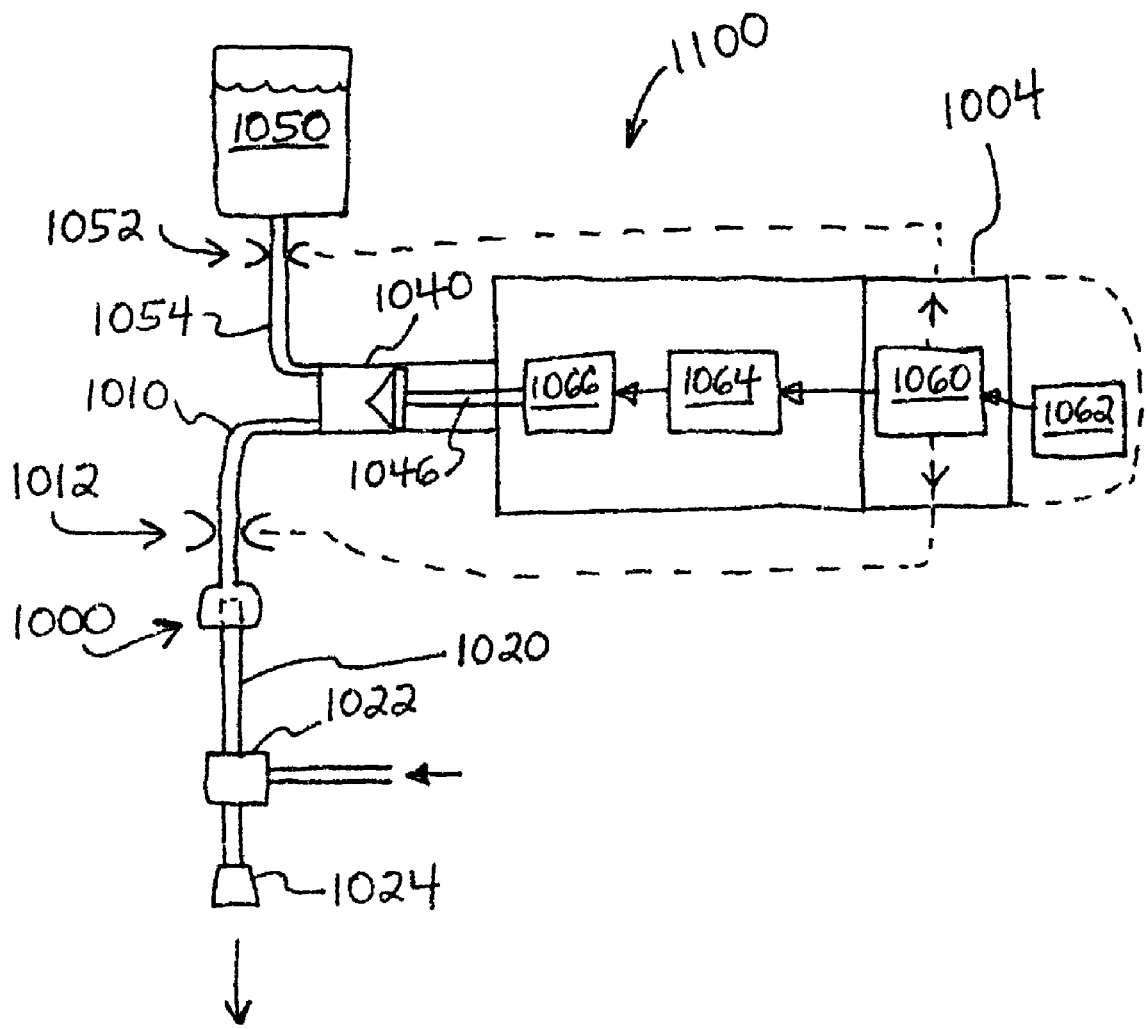
FIG. 10 is a schematic/block diagram showing a powered medical fluid injection system and a corresponding computer readable medium according to one embodiment.

FIG. 10 shows a schematic/block diagram of a powered medical fluid injection system according to certain embodiments of the invention. Also shown in FIG. 10 is a computer readable medium according to certain embodiments of the invention. A computer readable medium may, for example, contain instructions for causing a powered medical fluid injection system to perform one or more of the methods for removing air from a flow path, as described herein.

The medical fluid injection system 1100 shown in FIG. 10 comprises an injector head 1004, which may be adapted to receive a pressurizing unit 1040, such as a syringe, for example. In embodiments in which pressurizing unit 1040 comprises a syringe, for example, injector head 1004 may include an actuating mechanism 1046 (e.g., a plunger ram) and a source of motive force (e.g., motor 1066) for moving the actuating mechanism 1046, thereby causing the pressurizing unit 1040 to either receive a medical fluid (e.g., from reservoir 1050 via inlet tubing 1054), or deliver a medical fluid (e.g., via outlet tubing or proximal fluid conduit 1012).

In some embodiments, a proximal fluid conduit 1010 is operably engaged with an outlet of the pressurizing unit 1040. The proximal fluid conduit 1010 is adapted to be placed in fluid communication with a distal fluid conduit 1020 via a fluid connector 1000, thereby establishing a flow path. A valve 1012 is disposed along the proximal fluid conduit 1010 for providing fluid isolation. Valve 1012 may be a pinch valve, for example. In some embodiments, valve 1012 is a solenoid-operated pinch valve which may be designed to "fail shut," for example, upon a loss of power to the solenoid. Similarly, valve 1052 is disposed along inlet tubing 1054 to isolate the flow of fluid between reservoir 1050 and pressurizing unit 1040. Valve 1052 may also be a pinch valve according to some embodiments.

The injector head 1004 is adapted to perform a method of removing air from the flow path in response to a command from a user of the medical fluid injection system (e.g., a button press, or actuation of an item or icon within a user screen of a graphical user interface, for example). Such a method may be substantially similar to the methods described herein. For example, upon receiving an appropriate command from a user, the medical fluid injection system 1100 may, in sequence: deliver a first amount of a medical fluid from the pressurizing unit 1040 of the fluid injection system 1100 to the flow path; provide fluid isolation along the flow path between the fluid connector 1000 and the pressurizing unit 1040 (e.g., by closing valve 1012); create a vacuum in the pressurizing unit 1040 (e.g., by retracting an actuator 1046 within pressurizing unit 1040 (such as a plunger ram, for example); remove the fluid isolation (e.g., by opening valve 1012); and deliver a second amount of the medical fluid from the pressurizing unit 1040 to the flow path.

Instructions for performing a method of removing air from a flow path of fluid injection system 1100 may be stored in a computer readable medium 1062, as shown in FIG. 10. Computer readable medium 1062 may be housed within, or adjacent to, injector head 1004, as indicated by dotted lines in FIG. 10. Alternately, computer readable medium 1062 may be a separate component or element that is adapted to be placed in operable communication with processor 1060 such that instructions can be read from computer readable medium 1062 and subsequently executed by processor 1060. Examples of computer readable medium 1062 comprising such separate components or elements could include, but is not limited to, floppy disks and/or drives, CD-ROMs, DVDs, USB drives (e.g., "thumb" drives), etc. Such portable versions of computer readable medium 1062 could be inserted into a port on injector head 1004, for example, according to some embodiments.

As shown in FIG. 10, instructions received by processor 1060 from computer readable medium 1062 may cause processor 1060 to cause motor control circuit 1064 to actuate motor 1066 to move actuator 1046 to cause pressurizing unit 1040 to receive fluid (e.g., via reservoir 1050), deliver fluid (e.g., via proximal fluid conduit 1010), or, as appropriate, to create a vacuum in pressurizing unit 1040 (e.g., by retracting a plunger within pressurizing unit 1040 while valves 1052 and/or 1012 are in the shut position). Processor 1060 may also execute instructions received from computer readable medium 1062 to cause valves 1052 and 1012 to open or close as needed and when appropriate to perform the methods of removing air from a flow path described herein.

Various embodiments have been described herein. Further modifications and other embodiments will become apparent to those of ordinary skill in the art with the benefit of these teachings. Therefore, it is to be understood that the invention is not to be limited to the specific embodiments disclosed, and that modifications and other embodiments are intended to fall within the scope of the following claims. Although specific terms and examples may be employed herein, they are for purposes of illustration and not limitation.

What is claimed is:

1. A method of removing air bubbles from a flow path of a medical fluid injection system, the method comprising:
    establishing a flow path by placing a downstream fluid portion in fluid communication with an upstream fluid portion via a fluid connector, the upstream fluid portion being in fluid communication with a pressurizing unit of a medical fluid injection system;
    delivering a first amount of a medical fluid from the pressurizing unit to the flow path;
    providing fluid isolation between the fluid connector and the pressurizing unit;
    creating a vacuum in the pressurizing unit;
    removing the fluid isolation between the fluid connector and the pressurizing unit after creating the vacuum in the pressurizing unit; and
    delivering a second amount of the medical fluid from the pressurizing unit to the flow path.

2. The method of claim 1 wherein the fluid connector comprises a compression fitting between the upstream and downstream fluid portions.

3. The method of claim 1 wherein the fluid connector includes an o-ring that is compressed when the upstream and downstream fluid portions are placed in fluid communication.

4. The method of claim 1 wherein the pressurizing unit is a syringe having a chamber and a plunger adapted for movement within the chamber.

5. The method of claim 4 wherein creating the vacuum in the pressurizing unit comprises moving the plunger in a rearward direction within the chamber.

6. The method of claim 4 wherein delivering medical fluid to the flow path comprises moving the plunger in a forward direction within the chamber.

7. The method of claim 1 wherein fluid isolation is provided between the fluid connector and the pressurizing unit by closing a valve along the upstream fluid portion of the flow path.

8. The method of claim 7 wherein the upstream fluid portion comprises flexible tubing, and wherein the valve being closed is a pinch valve.

9. The method of claim 8 wherein removing the fluid isolation between the fluid connector and the pressurizing unit comprises opening the pinch valve.

10. The method of claim 1 wherein removing the fluid isolation between the fluid connector and the pressurizing unit causes air in the flow path to expand.

11. The method of claim 1 wherein removing the fluid isolation between the fluid connector and the pressurizing unit causes air bubbles at the fluid connector to expand and move toward the pressurizing unit.

12. The method of claim 1 wherein the vacuum created in the pressurizing unit causes air bubbles at the fluid connector to expand and move toward the pressurizing unit when the fluid isolation is removed.

13. A method of removing air bubbles from a flow path of a medical fluid injection system, the method comprising:
establishing a flow path by placing a downstream fluid portion in fluid communication with an upstream fluid portion via a fluid connector, the upstream fluid portion being in fluid communication with a pressurizing unit of a medical fluid injection system;
delivering a first amount of a medical fluid from the pressurizing unit to the flow path;
closing the flow path along the upstream fluid portion;
creating a vacuum in the pressurizing unit;
opening the flow path along the upstream fluid portion after creating the vacuum in the pressurizing unit; and
delivering a second amount of the medical fluid from the pressurizing unit to the flow path.

14. The method of claim 13 wherein the fluid connector comprises a sealing component.

15. The method of claim 14 wherein the sealing component comprises an o-ring that is compressed when the upstream and downstream fluid portions are placed in fluid communication.

16. The method of claim 13 wherein the pressurizing unit is a syringe having a chamber and a plunger adapted for movement within the chamber.

17. The method of claim 16 wherein creating the vacuum in the pressurizing unit comprises retracting the plunger within the chamber.

18. The method of claim 16 wherein delivering the first and second amounts of medical fluid to the flow path comprises advancing the plunger within the chamber.

19. The method of claim 13 wherein the flow path is closed along the upstream fluid portion by closing a valve.

20. The method of claim 19 wherein the upstream fluid portion comprises flexible tubing, and wherein the valve being closed is a pinch valve.

21. The method of claim 20 wherein opening the flow path along the upstream fluid portion comprises opening the pinch valve.

22. The method of claim 13 wherein opening the flow path along the upstream fluid portion causes air in the flow path to expand.

23. The method of claim 13 wherein opening the flow path along the upstream fluid portion causes air bubbles at the fluid connector to expand and move toward the pressurizing unit.

24. The method of claim 13 wherein the vacuum created in the pressurizing unit causes air bubbles at the fluid connector to expand and move toward the pressurizing unit when the flow path is opened along the upstream portion.

25. A method of removing air bubbles from a flow path of a medical fluid injection system, the method comprising:
establishing a flow path in a medical fluid injection system, the flow path comprising
a first pressurizing unit adapted to hold a first medical fluid,
a first proximal fluid conduit connected to an outlet of the first pressurizing unit,
a first distal fluid conduit connected to the first proximal fluid conduit via a first fluid connector disposed therebetween,
a second pressurizing unit adapted to hold a second medical fluid,
a second proximal fluid conduit connected to an outlet of the second pressurizing unit, and
a second distal fluid conduit connected to the second proximal fluid conduit via a second fluid connector disposed therebetween;
delivering a first amount of the first medical fluid from the first pressurizing unit to the first distal fluid conduit;
delivering a second amount of the second medical fluid from the second pressurizing unit to the second distal fluid conduit;
closing the flow path along the first and second proximal fluid conduits;
creating a vacuum in the first and second pressurizing units;
opening the flow path along the first and second proximal fluid conduits after creating the vacuum in the first and second pressurizing units;
delivering a third amount of the first medical fluid from the first pressurizing unit to the first distal fluid conduit; and
delivering a fourth amount of the second medical fluid from the second pressurizing unit to the second distal fluid conduit.

26. The method of claim 25 wherein opening the flow path comprises opening a valve along at least one of the first and second proximal fluid conduits.

27. The method of claim 26 wherein the first and second proximal fluid conduits comprise flexible tubing, and wherein opening the flow path comprises opening a pinch valve disposed along at least one of the first and second proximal fluid conduits.

28. The method of claim 25 wherein the flow path further comprises a multi-port valve having two inlet ports adapted to receive the first and second medical fluids from the first and second distal fluid conduits, the multi-port valve also having an outlet port adapted to selectively deliver only one of the first or the second medical fluids.

29. The method of claim 28 wherein delivering the first amount of the first medical fluid substantially fills the flow path from the first pressurizing unit at least partially into the first distal fluid conduit, and wherein delivering the second amount of the second medical fluid substantially fills the flow path from the second pressurizing unit at least partially into the second distal conduit.

30. The method of claim 29 wherein delivering the third amount of the first medical fluid substantially fills the flow path with the first medical fluid from the first pressurizing unit to the outlet port of the multi-port valve, and wherein delivering the fourth amount of the second medical fluid substantially fills the flow path with the second medical fluid from the second pressurizing unit to the outlet port of the multi-port valve.

31. The method of claim 25 further comprising:
pausing after delivering the fourth amount of the second medical fluid; and
delivering a fifth amount of the second medical fluid from the second pressurizing unit.

32. A computer readable medium comprising computer executable instructions adapted to cause a fluid injection system to perform a method of removing air from a flow path of the fluid injection system, the method comprising:
delivering a first amount of a medical fluid from a pressurizing unit of the fluid injection system to the flow path, the flow path comprising an upstream portion and a downstream portion fluidly coupled via a fluid connector disposed therebetween;

providing fluid isolation along the flow path between the fluid connector and the pressurizing unit;

creating a vacuum in the pressurizing unit;

removing the fluid isolation after creating the vacuum in the pressurizing unit; and delivering a second amount of the medical fluid from the pressurizing unit to the flow path.

33. The computer readable medium of claim 32 wherein the method of removing air is performed in response to an input from a user of the fluid injection system.

34. A computer readable medium comprising computer executable instructions adapted to cause a fluid injection system to perform a method of removing air from a flow path of the fluid injection system, the method comprising:

delivering a first amount of a first medical fluid from a first pressurizing unit of the fluid injection system to a first distal fluid conduit of the flow path;

delivering a second amount of a second medical fluid from a second pressurizing unit of the fluid injection system to a second distal fluid conduit of the flow path;

closing the flow path along the first and second proximal fluid conduits;

creating a vacuum in the first and second pressurizing units;

opening the flow path along the first and second proximal fluid conduits after creating the vacuum in the first and second pressurizing units;

delivering a third amount of the first medical fluid from the first pressurizing unit to the first distal fluid conduit; and delivering a fourth amount of the second medical fluid from the second pressurizing unit to the second distal fluid conduit.

35. The computer readable medium of claim 34 wherein the method of removing air is performed in response to an input from a user of the fluid injection system.

36. A medical fluid injection system comprising:

an injector head comprising a pressurizing unit and a source of motive force for causing the pressurizing unit to receive and/or deliver a medical fluid;

a proximal fluid conduit operably engaged with an outlet of the pressurizing unit, the proximal fluid conduit being adapted to be placed in fluid communication with a distal fluid conduit via a fluid connector, thereby establishing a flow path; and a valve for providing fluid isolation along the proximal fluid conduit;

wherein the injector head is adapted to perform a method of removing air from the flow path in response to a command from a user of the medical fluid injection system, the method comprising:

delivering a first amount of a medical fluid from a pressurizing unit of the fluid injection system to the flow path, the flow path comprising an upstream portion and a downstream portion fluidly coupled via a fluid connector disposed therebetween;

providing fluid isolation along the flow path between the fluid connector and the pressurizing unit;

creating a vacuum in the pressurizing unit;

removing the fluid isolation after creating the vacuum in the pressurizing unit; and delivering a second amount of the medical fluid from the pressurizing unit to the flow path.

37. The medical fluid injection system of claim 36 wherein the injector head further comprises a processor adapted to receive executable instructions for performing the method of removing air from a computer readable medium.

38. The medical fluid injection system of claim 37 wherein the computer readable medium is housed within the injector head.

* * * * *